(12) United States Patent
Mattivi et al.

(10) Patent No.: US 11,574,128 B2
(45) Date of Patent: Feb. 7, 2023

(54) METHOD, APPARATUS AND COMPUTER PROGRAM PRODUCT FOR GENERATING MULTI-PARADIGM FEATURE REPRESENTATIONS

(71) Applicant: Optum Services (Ireland) Limited, Dublin (IE)

(72) Inventors: Riccardo Mattivi, Dublin (IE); Houssem Chatbri, Dublin (IE); Ahmed Selim, Dublin (IE)

(73) Assignee: OPTUM SERVICES (IRELAND) LIMITED, Dublin (IE)

( * ) Notice: Subject to any disclaimer, the term of this patent is extended or adjusted under 35 U.S.C. 154(b) by 255 days.

(21) Appl. No.: 16/946,175

(22) Filed: Jun. 9, 2020

(65) Prior Publication Data
US 2021/0383068 A1 Dec. 9, 2021

(51) Int. Cl.
*G06F 40/30* (2020.01)
*G16H 40/20* (2018.01)
(Continued)

(52) U.S. Cl.
CPC .......... *G06F 40/30* (2020.01); *G06F 16/9024* (2019.01); *G06F 17/16* (2013.01);
(Continued)

(58) Field of Classification Search
CPC ...... G06F 40/30; G06F 16/9024; G06F 17/16; G06F 40/20; G06F 16/38; G06N 20/00;
(Continued)

(56) References Cited

U.S. PATENT DOCUMENTS 7,177,798 B2   2/2007  Hsu et al.
10,187,399 B2  1/2019  Katz
(Continued)

FOREIGN PATENT DOCUMENTS

CN      105894088 A     8/2016
WO      2017/161316 A1  9/2017

OTHER PUBLICATIONS

Chen, Yuwen, and Jiangtao Ren. "Automatic ICD code assignment utilizing textual descriptions and hierarchical structure of ICD code." 2019 IEEE International Conference on Bioinformatics and Biomedicine (BIBM). IEEE, 2019. (Year: 2019).*
(Continued)

*Primary Examiner* — Soe Hlaing
(74) *Attorney, Agent, or Firm* — Alston & Bird LLP

(57) ABSTRACT

Methods, apparatus, systems, computing devices, computing entities, and/or the like for programmatically generating multi-paradigm feature representations are provided. An example method may include generating a code dataset including a plurality of codes associated with a predictive entity; generating a plurality of semantic feature vectors based at least in part on code description metadata; generating a plurality of structural feature vectors based at least in part on code relation metadata; generating a plurality of multi-paradigm feature vectors based at least in part on the plurality of semantic feature vectors and the plurality of structural feature vectors; generating a prediction for the predictive entity by processing the plurality of multi-paradigm feature vectors using a prediction model; and performing one or more prediction-based actions based on the prediction.

18 Claims, 11 Drawing Sheets

(51) Int. Cl.
    *G06N 20/00*        (2019.01)
    *G06F 16/901*      (2019.01)
    *G06F 40/20*        (2020.01)
    *G06F 17/16*        (2006.01)

(52) U.S. Cl.
    CPC .............. *G06F 40/20* (2020.01); *G06N 20/00* (2019.01); *G16H 40/20* (2018.01)

(58) Field of Classification Search
    CPC ........ G06N 3/08; G06N 5/022; G06N 3/0454; G16H 40/20
    See application file for complete search history.

(56) References Cited

U.S. PATENT DOCUMENTS

| | | | |
|---|---|---|---|
| 10,360,507 | B2 | 7/2019 | Aravamudan et al. |
| 10,402,909 | B1 | 9/2019 | Khalak et al. |
| 10,459,962 | B1 | 10/2019 | Jayaraman et al. |
| 11,222,031 | B1 * | 1/2022 | Mohandas .............. G06F 40/30 |
| 2003/0217052 | A1 | 11/2003 | Rubenczyk et al. |
| 2019/0057774 | A1 | 2/2019 | Velez et al. |
| 2019/0130025 | A1 | 5/2019 | Crudele et al. |
| 2020/0057946 | A1 | 2/2020 | Singaraju et al. |
| 2020/0184016 | A1 | 6/2020 | Roller |
| 2020/0226321 | A1 | 7/2020 | Bums et al. |
| 2020/0311262 | A1 | 10/2020 | Nguyen et al. |
| 2021/0012215 | A1 | 1/2021 | Fei et al. |
| 2021/0042586 | A1 | 2/2021 | Toyoshiba |
| 2021/0295822 | A1 | 9/2021 | Tomkins et al. |
| 2021/0383070 | A1 | 12/2021 | Hunter |

OTHER PUBLICATIONS

Teng, Fei, et al. "Automatic medical code assignment via deep learning approach for intelligent healthcare." IEEE journal of biomedical and health informatics 24.9 (2020): 2506-2515. (Year: 2020).*

Bordes, Antoine et al. "Translating Embeddings For Modeling Multi-Relational Data," Advances On Neural Information Processing Systems: Proceedings of the 26th International Conference on Neural Information Processing Systems, vol. 2, Dec. 2013, (9 pages), DOI: 10.5555/2999792.2999923.

Le, Quoc et al. "Distributed Representations of Sentences and Documents," Proceedings of the 31st International Conference on Machine Learning, PMLR, vol. 32, No. 2, Jun. 18, 2014 (9 pages).

Ling, Yuan Ling et al. "Integrating Extra Knowledge Into Word Embedding Models For Biomedical NLP Tasks," In 2017 International Joint Conference on Neural Networks (IJCNN), May 14, 2017 (8 pages), IEEE.

Mai, Gengchen et al. "Combining Text Embedding and Knowledge Graph Embedding Techniques for Academic Search Engines," In Semdeep/NLIWoD@ ISWC, Oct. 2018, pp. 77-88.

Mikolov Tomas et al. "Distributed Representations of Words and Phrases and Their Compositionality," In Advances In Neural Information Processing Systems 26, 27th Annual Conference on Neural Information Processing Systems (2013), (9 pages).

Sun, Haixia et al. "Medical Knowledge Graph To Enhance Fraud, Waste, and Abuse Detection On Claim Data: Model Development ad Performance Evaluation," JMIR Medical Informatics, Jul. 2020, vol. 8, No. 7:e17653, Published Online Jul. 23, 2020, (26 pages), DOI: 10.2196/17653, PMCID: PMC7413281, PMID: 32706714.

Trouillon, Théo et al. "Complex Embeddings For Simple Link Prediction," In International Conference on Machine Learning, Jun. 11, 2016, (10 pages).

Wang, Zhen et al. "Knowledge Graph Embedding by Translating on Hyperplanes," Proceedings of the Twenty-Eighth AAAI Conference On Artificial Intelligence, vol. 28, No. 1, pp. 1112-1119, Jun. 21, 2014, DOI: 10.5555/2893873.2894046.

Yang, Bishan et al. "Embedding Entities and Relations for Learning and Inference In Knowledge Bases," ICLR (Poster) 2015, arXiv:1412.6575v4 [cs.CL] Aug. 29, 2015, (12 pages).

Islam, Saiful, et al., "A Systematic Review on Healthcare Analytics: Application and Theoretical Perspective of Data Mining", May 23, 2018, Healthcare, 43 pages, 6, 54, www.mdpi.com/journal/healthcare.

NonFinal Office Action for U.S. Appl. No. 17/466,594, dated Dec. 6, 2022, (8 pages), United States Patent and Trademark Office, US.

* cited by examiner

US 11,574,128 B2

METHOD, APPARATUS AND COMPUTER PROGRAM PRODUCT FOR GENERATING MULTI-PARADIGM FEATURE REPRESENTATIONS

TECHNOLOGICAL FIELD

Embodiments of the present disclosure generally relate to generating feature representations. For example, various embodiments of the present disclosure may programmatically generate multi-paradigm feature representations for medical codes.

BACKGROUND

Computer algorithms (for example, machine learning models and/or artificial intelligence programs) may be implemented to analyze trends and/or patterns in the data. For example, prediction models may analyze data related to medical claims for the purpose of identifying potential healthcare fraud, waste, abuse, error (FWAE), predicting disease progression, and/or the like.

Raw data may need to be transformed and/or converted to feature representations that are recognizable by and compatible with prediction models in order to be provided as input data. Applicant has identified many technical challenges, deficiencies and problems associated with transforming and/or converting raw data. For example, many techniques do not fully capture all the intrinsic properties of raw data, resulting in information loss during transformation/conversion and inaccurate outputs from the corresponding prediction models.

BRIEF SUMMARY

In general, embodiments of the present disclosure provide methods, apparatus, systems, computing devices, computing entities, and/or the like.

In accordance with one aspect, an apparatus for programmatically generating multi-paradigm feature representations is provided. The apparatus may comprise at least one processor and at least one non-transitory memory comprising a computer program code. The at least one non-transitory memory and the computer program code may be configured to, with the at least one processor, cause the apparatus to: generate a code dataset comprising a plurality of codes associated with a predictive entity, wherein the plurality of codes are associated with code description metadata and code relation metadata, wherein (i) the code description metadata for a code comprises a textual description of the code and (ii) the code relation metadata describes one or more relationships between the plurality of codes; generate, by processing the code description metadata for each code of the plurality of codes using a semantic machine learning model, a plurality of semantic feature vectors based at least in part on the code description metadata, wherein: (i) the plurality of semantic feature vectors comprise a semantic feature vector for each code of the plurality of codes, and (ii) each semantic feature vector that is associated with a code comprises numeric representations of one or more phrases used in the textual description for the code; generate, by processing the code relation metadata using a structural machine learning model, a plurality of structural feature vectors based at least in part on the code relation metadata; generate a plurality of multi-paradigm feature vectors based at least in part on the plurality of semantic feature vectors and the plurality of structural feature vectors; generate a prediction for the predictive entity by processing the plurality of multi-paradigm feature vectors using a prediction model; and perform one or more prediction-based actions based on the prediction.

In some examples, the plurality of codes may be associated with a plurality of medical codes.

In some examples, the plurality of medical codes may be associated with a same coding system.

In some examples, a first portion of the plurality of medical codes may be associated with a first coding system. In some examples, a second portion of the plurality of medical codes may be associated with a second coding system different from the first coding system.

In some examples, the semantic machine learning model may comprise at least one natural language processing (NLP) machine learning model.

In some examples, the at least one non-transitory memory and the computer program code may be configured to, with the at least one processor, cause the apparatus to further: possess the textual description of the code using, for example, a Word2Vec model; and possess the textual description of the code using, for example, a Sentence2Vec model. While the above description uses the Word2Vec model and the Sentence2Vec model as examples, it is noted that the scope of the present disclosure is not limited to these models only. Additionally, or alternatively, other models and/or techniques may be implemented for the semantic machine learning model, including, but not limited to, generic language model(s) and/or natural language processing technique(s), FastText approach (based on subwords information), Bidirectional Encoder Representations from Transformers (BERT) model, Biomedical Bidirectional Encoder Representations from Transformers (BioBERT) model, and/or the like.

In some examples, the at least one non-transitory memory and the computer program code may be configured to, with the at least one processor, cause the apparatus to further: generate a semantic feature space comprising a plurality of semantic feature nodes based at least in part on the plurality of semantic feature vectors, wherein each of the plurality of semantic feature nodes is associated with a corresponding code of the plurality of codes, wherein proximities between the plurality of semantic feature nodes are based at least in part on a similarity level associated with the textual description of each corresponding code.

In some examples, the structural machine learning model may comprise a graph machine learning model.

In some examples, the at least one non-transitory memory and the computer program code may be configured to, with the at least one processor, cause the apparatus to further: generate a structural feature space comprising a plurality of structural feature nodes based at least in part on the plurality of structural feature vectors, wherein each of the plurality of structural feature nodes is associated with a corresponding code of the plurality of codes, wherein proximities between the plurality of structural feature nodes are based at least in part on the one or more relationships described in the code relation metadata.

In some examples, when generating the plurality of multi-paradigm feature vectors, the at least one non-transitory memory and the computer program code may be configured to, with the at least one processor, cause the apparatus to further: merge the plurality of semantic feature vectors and the plurality of structural feature vectors.

In accordance with one aspect, a computer-implemented method for programmatically generating multi-paradigm feature representations may be provided. The computer-implemented method may comprise generating, by processing the code description metadata for each code of the plurality of codes using a semantic machine learning model, a plurality of semantic feature vectors based at least in part on the code description metadata, wherein: (i) the plurality of semantic feature vectors comprise a semantic feature vector for each code of the plurality of codes, and (ii) each semantic feature vector that is associated with a code comprises numeric representations of one or more phrases used in the textual description for the code; generating, by processing the code relation metadata using a structural machine learning model, a plurality of structural feature vectors based at least in part on the code relation metadata; generating a plurality of multi-paradigm feature vectors based at least in part on the plurality of semantic feature vectors and the plurality of structural feature vectors; generating a prediction for the predictive entity by processing the plurality of multi-paradigm feature vectors using a prediction model; and performing one or more prediction-based actions based on the prediction.

In accordance with one aspect, a computer program product for programmatically generating multi-paradigm feature representations may be provided. The computer program product may comprise at least one non-transitory computer-readable storage medium having computer-readable program code portions stored therein. The computer-readable program code portions may comprise an executable portion configured to: generate a code dataset comprising a plurality of codes associated with a predictive entity, wherein the plurality of codes are associated with code description metadata and code relation metadata, wherein (i) the code description metadata for a code comprises a textual description of the code and (ii) the code relation metadata describes one or more relationships between the plurality of codes; generate, by processing the code description metadata for each code of the plurality of codes using a semantic machine learning model, a plurality of semantic feature vectors based at least in part on the code description metadata, wherein: (i) the plurality of semantic feature vectors comprise a semantic feature vector for each code of the plurality of codes, and (ii) each semantic feature vector that is associated with a code comprises numeric representations of one or more phrases used in the textual description for the code; generate, by processing the code relation metadata using a structural machine learning model, a plurality of structural feature vectors based at least in part on the code relation metadata; generate a plurality of multi-paradigm feature vectors based at least in part on the plurality of semantic feature vectors and the plurality of structural feature vectors; generate a prediction for the predictive entity by processing the plurality of multi-paradigm feature vectors using a prediction model; and perform one or more prediction-based actions based on the prediction.

The above summary is provided merely for purposes of summarizing some example embodiments to provide a basic understanding of some aspects of the disclosure. Accordingly, it will be appreciated that the above-described embodiments are merely examples. It will be appreciated that the scope of the disclosure encompasses many potential embodiments in addition to those here summarized, some of which will be further described below.

BRIEF DESCRIPTION OF THE SEVERAL VIEWS OF THE DRAWING(S)

Having thus described the disclosure in general terms, reference will now be made to the accompanying drawings, which are not necessarily drawn to scale, and wherein:

Figure 7:
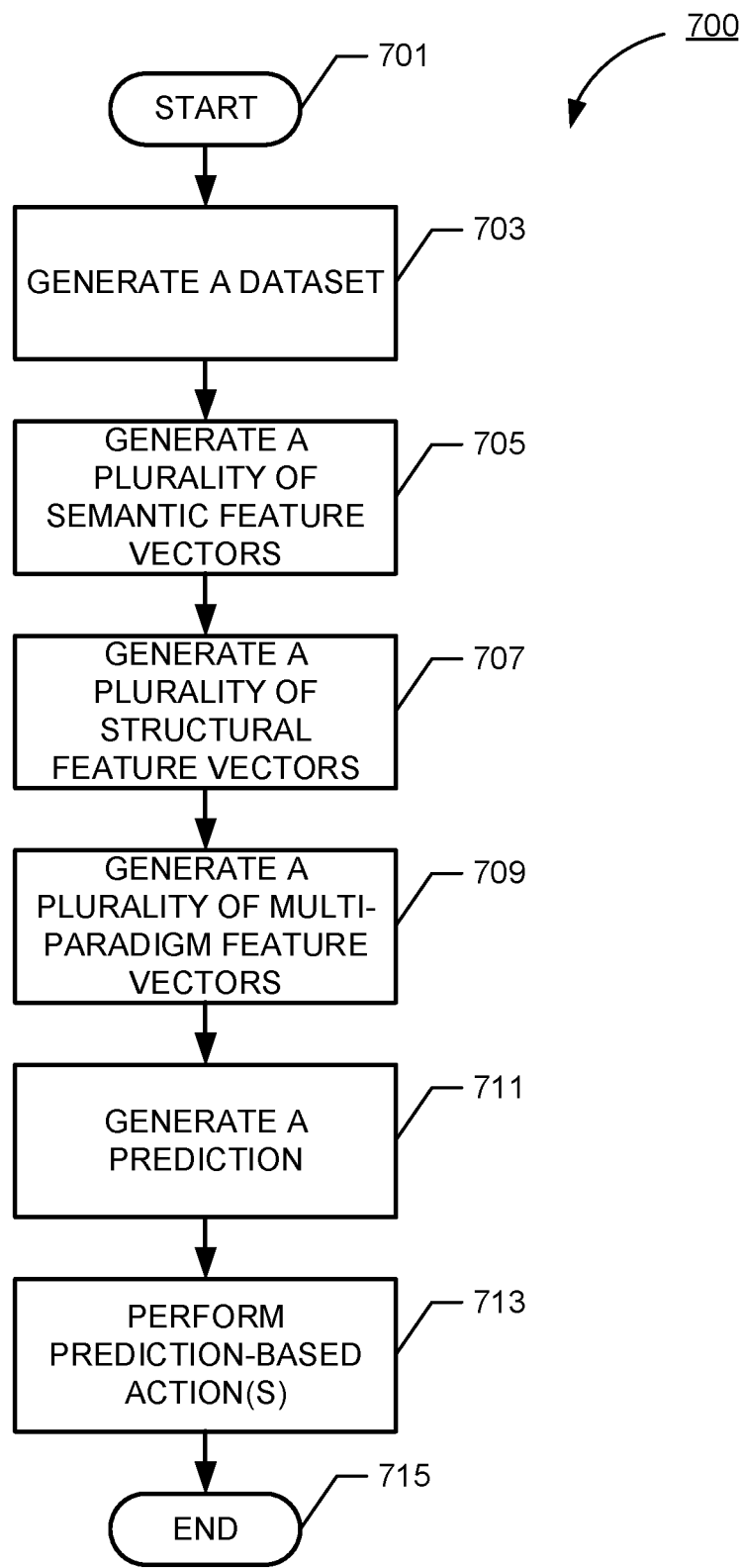
Figure 8:
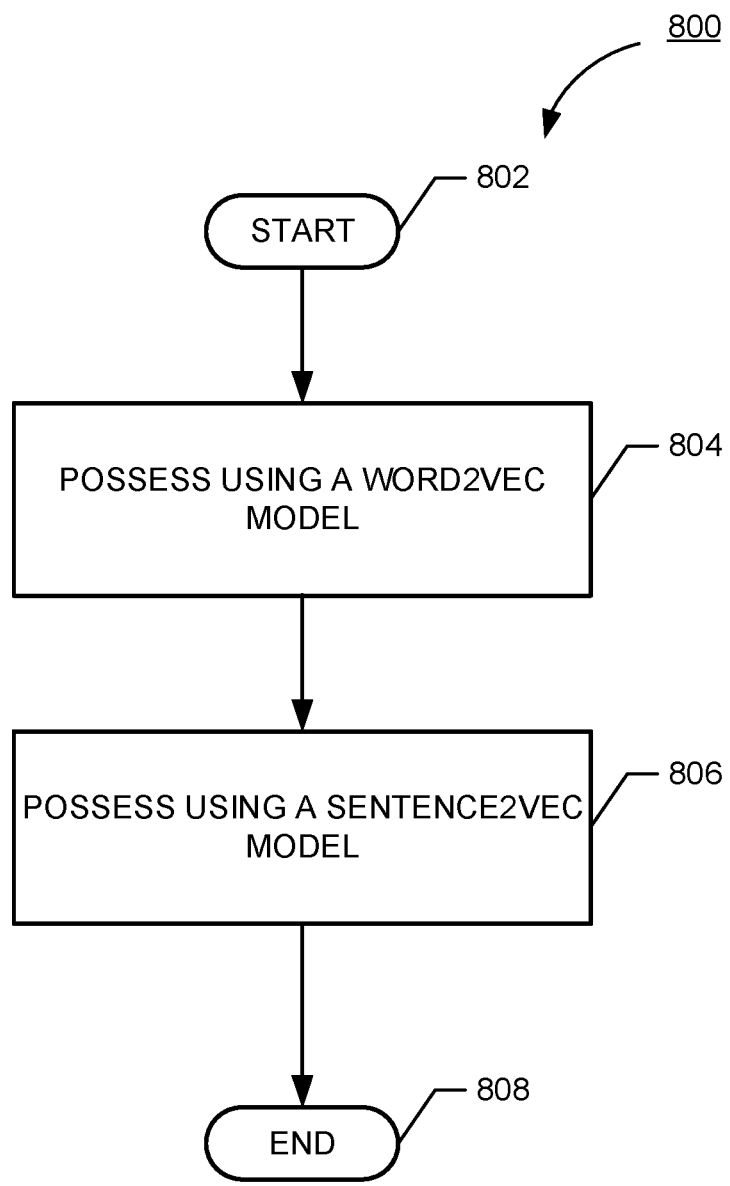
Figure 9:
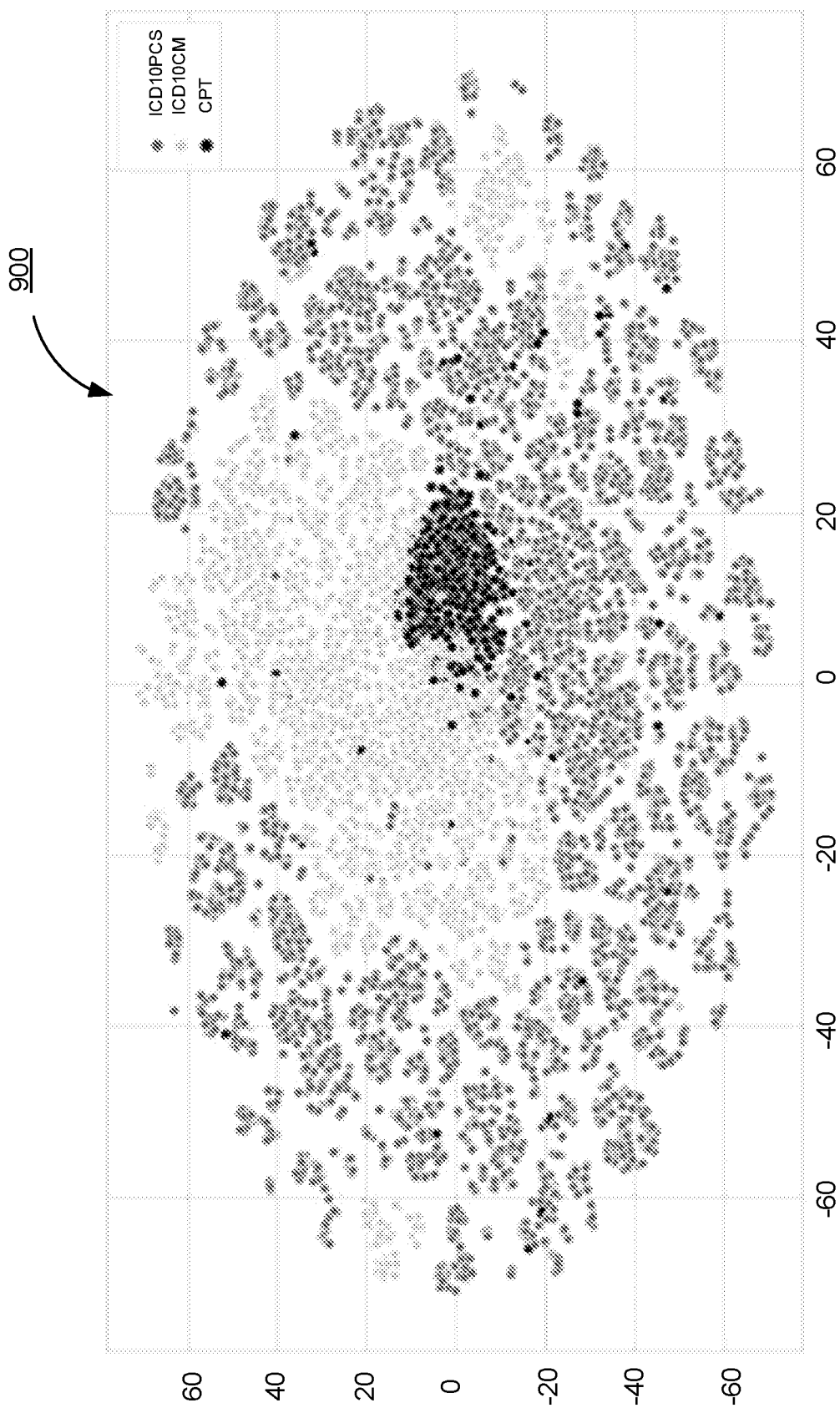
Figure 10:
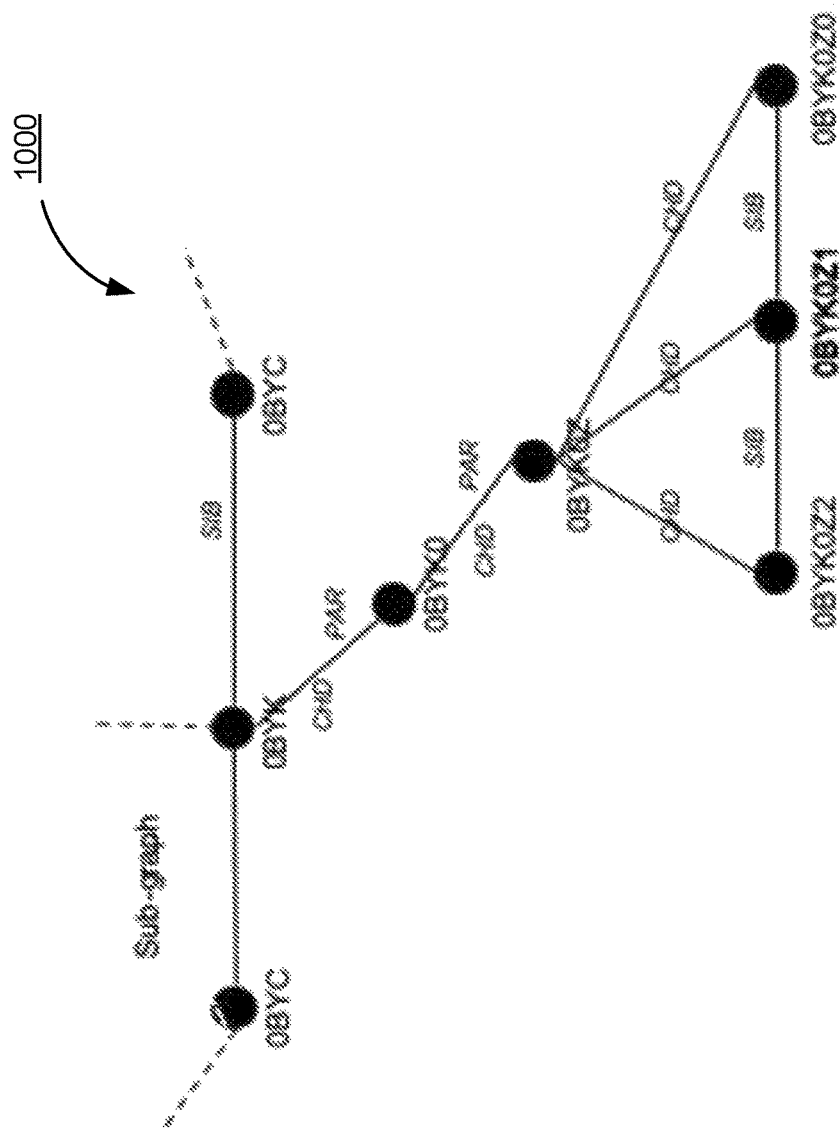
Figure 11:
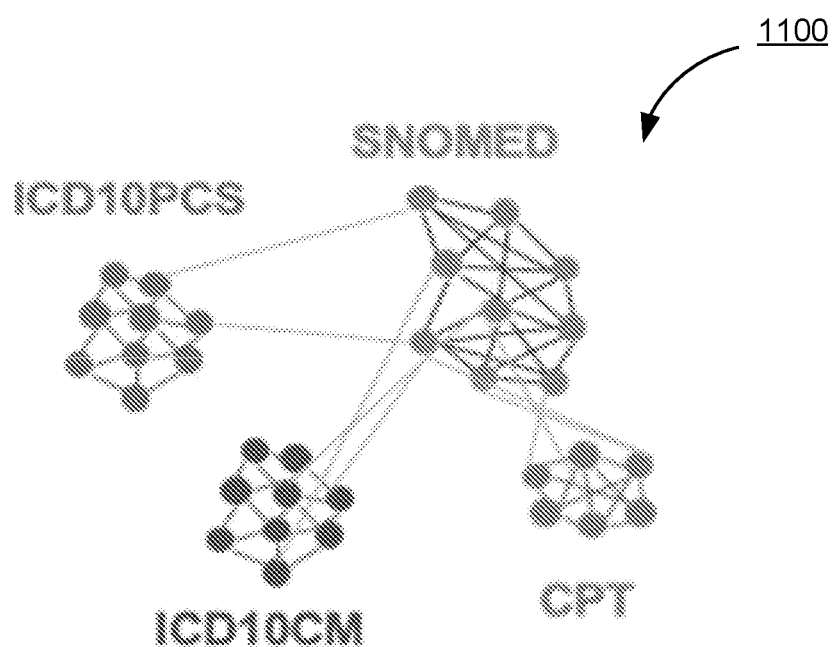
Figure 12:
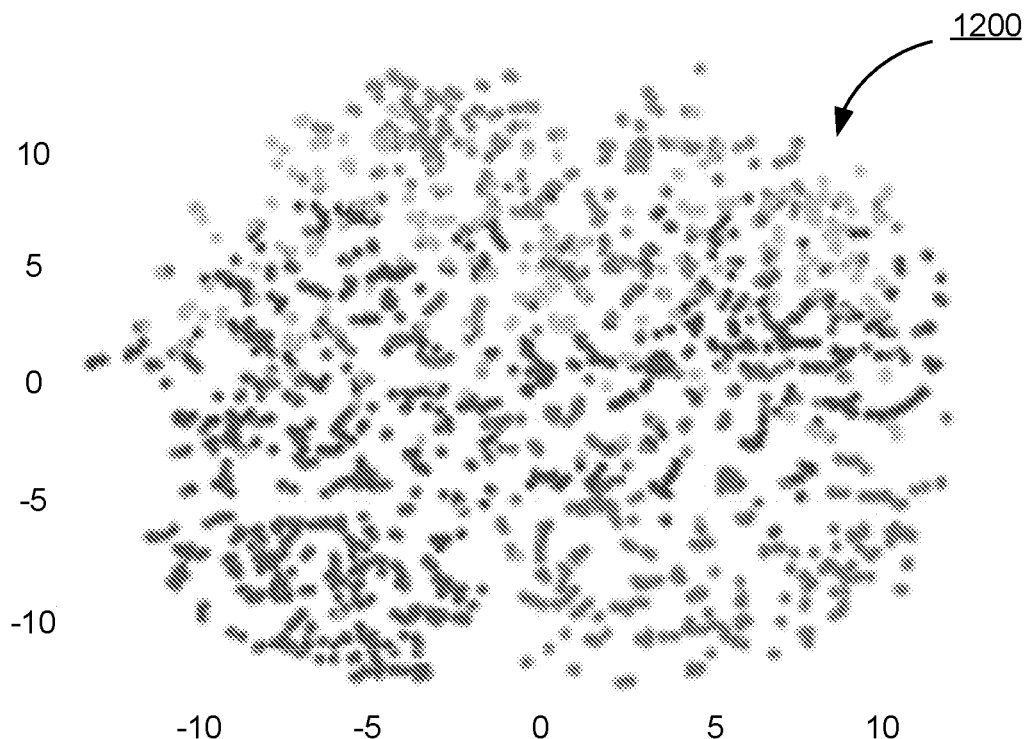
Figure 13:
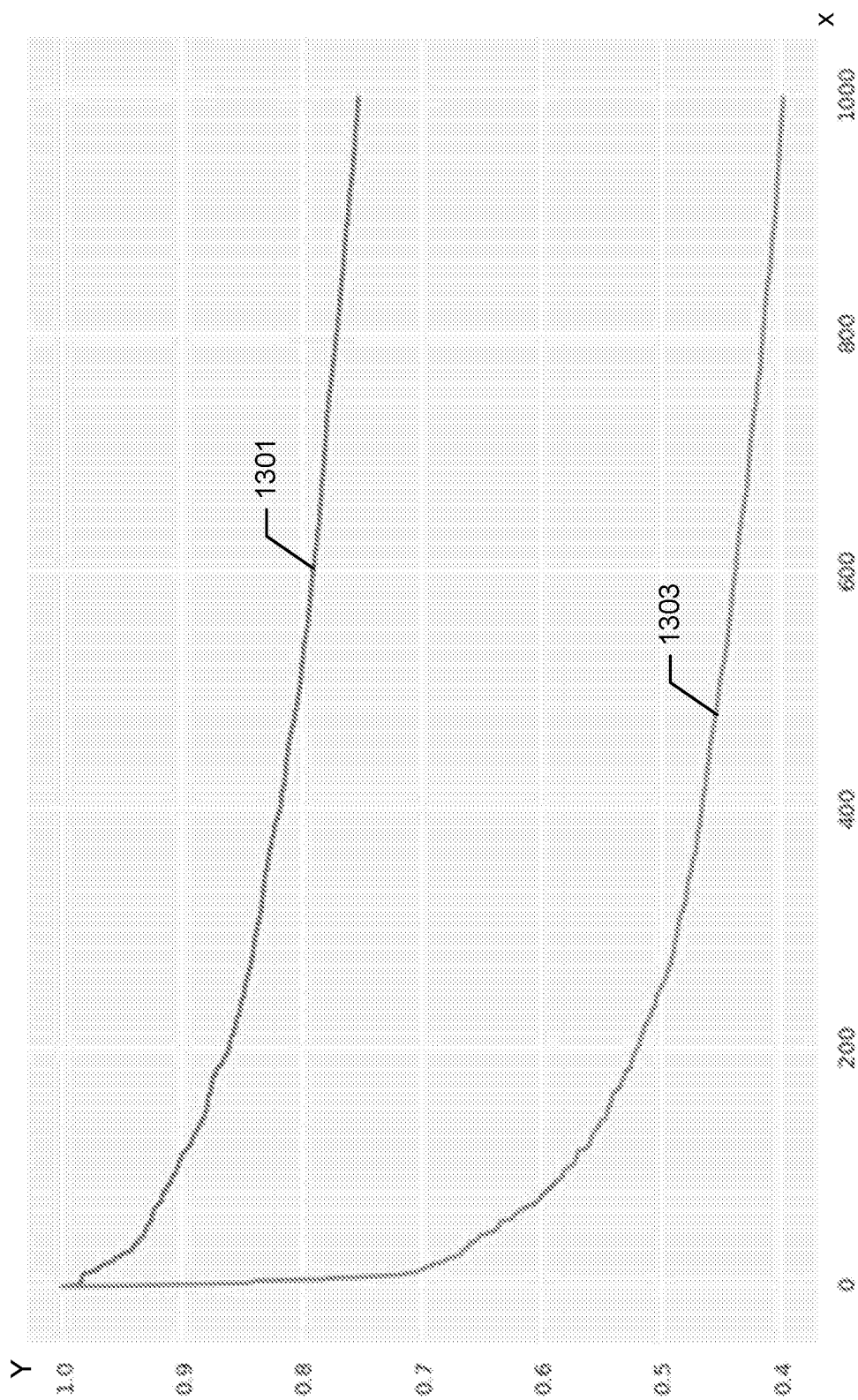

FIG. 7 and FIG. 8 provide example flowcharts illustrating example steps, processes, procedures, and/or operations associated with an example feature representation generating platform/system in accordance with various embodiments of the present disclosure;

FIG. 9 illustrates an example feature space in accordance with various embodiments of the present disclosure;

FIG. 10 and FIG. 11 are example hierarchical visualizations of example code datasets in accordance with various embodiments of the present disclosure;

FIG. 12 illustrates an example feature space in accordance with various embodiments of the present disclosure; and FIG. 13 illustrates example performance curves associated with prediction models in accordance with various embodiments of the present disclosure.

DETAILED DESCRIPTION OF SOME EXAMPLE EMBODIMENTS

Various embodiments of the present disclosure now will be described more fully hereinafter with reference to the accompanying drawings, in which some, but not all embodiments of the disclosure are shown. Indeed, this disclosure may be embodied in many different forms and should not be construed as limited to the embodiments set forth herein; rather, these embodiments are provided so that this disclosure will satisfy applicable legal requirements. The term "or" (also designated as "/") is used herein in both the alternative and conjunctive sense, unless otherwise indicated. The terms "illustrative" and "exemplary" are used to be examples with no indication of quality level. Like numbers refer to like elements throughout.

The phrases "in one embodiment," "according to one embodiment," and/or the like generally mean that the particular feature, structure, or characteristic following the phrase may be included in at least one embodiment of the present disclosure and may be included in more than one embodiment of the present disclosure (importantly, such phrases do not necessarily refer to the same embodiment).

I. COMPUTER PROGRAM PRODUCTS, METHODS, AND COMPUTING ENTITIES

Embodiments of the present disclosure may be implemented as computer program products that comprise articles of manufacture. Such computer program products may include one or more software components including, for example, applications, software objects, methods, data structures, and/or the like. A software component may be coded in any of a variety of programming languages. An illustrative programming language may be a lower-level programming language such as an assembly language associated with a particular hardware architecture and/or operating system platform/system. A software component comprising assembly language instructions may require conversion into executable machine code by an assembler prior to execution by the hardware architecture and/or platform/system. Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query or search language, and/or a report writing language. In one or more example embodiments, a software component comprising instructions in one of the foregoing examples of programming languages may be executed directly by an operating system or other software component without having to be first transformed into another form. A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

Additionally, or alternatively, embodiments of the present disclosure may be implemented as a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media may include all computer-readable media (including volatile and non-volatile media).

In one embodiment, a non-volatile computer-readable storage medium may include a floppy disk, flexible disk, hard disk, solid-state storage (SSS) (e.g., a solid-state drive (SSD), solid state card (SSC), solid state module (SSM), enterprise flash drive, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magnetoresistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In one embodiment, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present disclosure may also be implemented as methods, apparatus, systems, computing devices, computing entities, and/or the like. As such, embodiments of the present disclosure may take the form of a data structure, apparatus, system, computing device, computing entity, and/or the like executing instructions stored on a computer-readable storage medium to perform certain steps or operations. Thus, embodiments of the present disclosure may also take the form of an entirely hardware embodiment, an entirely computer program product embodiment, and/or an embodiment that comprises combination of computer program products and hardware performing certain steps or operations.

Embodiments of the present disclosure are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatus, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some exemplary embodiments, retrieval, loading, and/or execution may be performed in parallel such that multiple instructions are retrieved, loaded, and/or executed together. Thus, such embodiments can produce specifically-configured machines performing the steps or operations specified in the block diagrams and flowchart illustrations. Accordingly, the block diagrams and flowchart illustrations support various combinations of embodiments for performing the specified instructions, operations, or steps.

II. EXEMPLARY SYSTEM ARCHITECTURE

Figure 1:
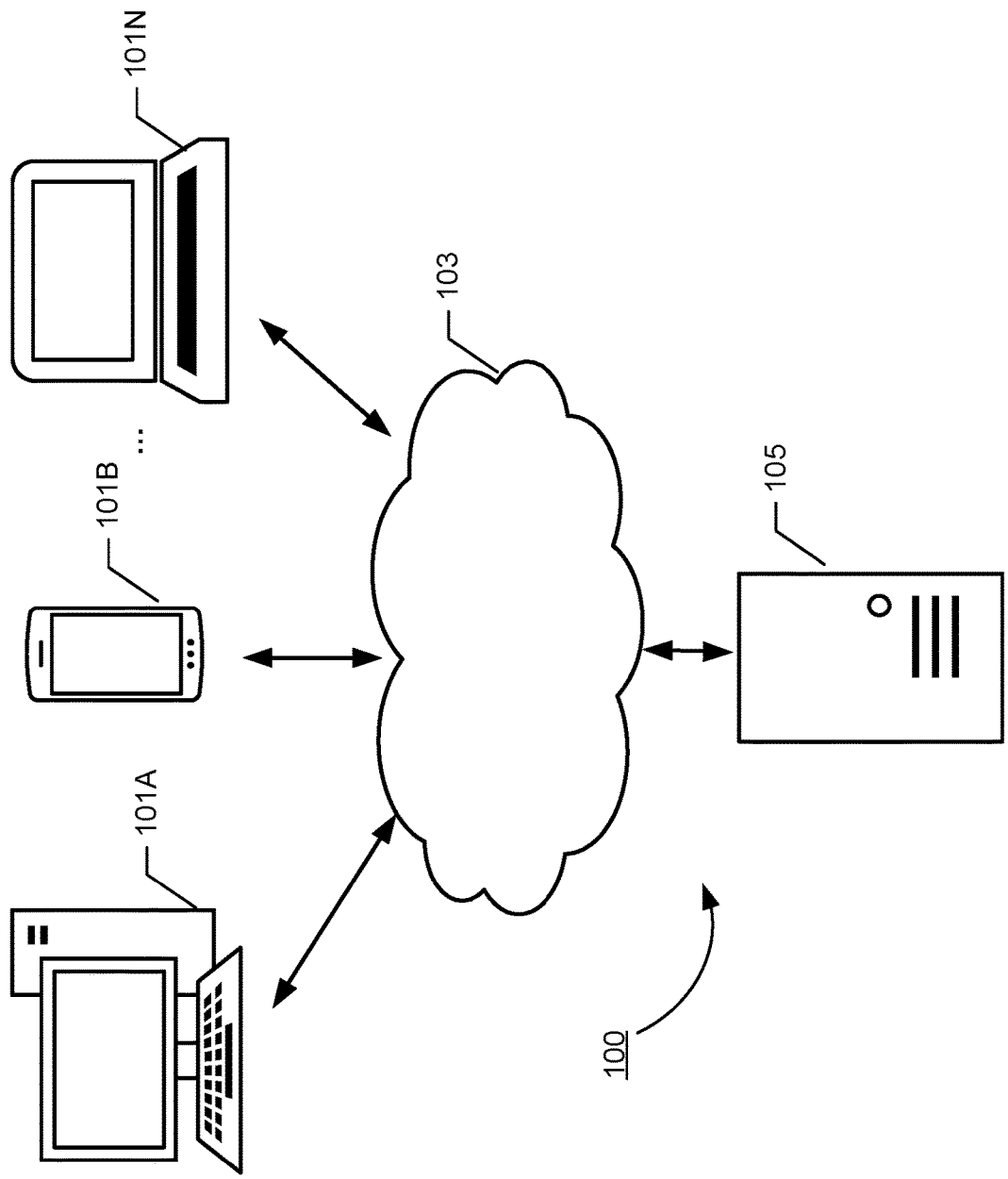
FIG. 1 is an example diagram of an example feature representation generating platform/system that can be used in accordance with various embodiments of the present disclosure.

FIG. 1 provides an illustration of a feature representation generating platform/system 100 that can be used in conjunction with various embodiments of the present disclosure. As shown in FIG. 1, the feature representation generating platform/system 100 may comprise one or more feature representation computing entities 105, one or more user computing entities 101A, 101B, ... 101N, and one or more networks 103. Each of the components of the feature representation generating platform/system 100 may be in electronic communication with, for example, one another over the same or different networks 103 that are wireless or wired networks including, for example, a wired or wireless Personal Area Network (PAN), Local Area Network (LAN), Metropolitan Area Network (MAN), Wide Area Network (WAN), and/or the like. Additionally, while FIG. 1 illustrates certain system entities as separate, standalone entities, the various embodiments are not limited to this particular architecture.

A. Exemplary Feature Representation Computing Entity

Figure 2:
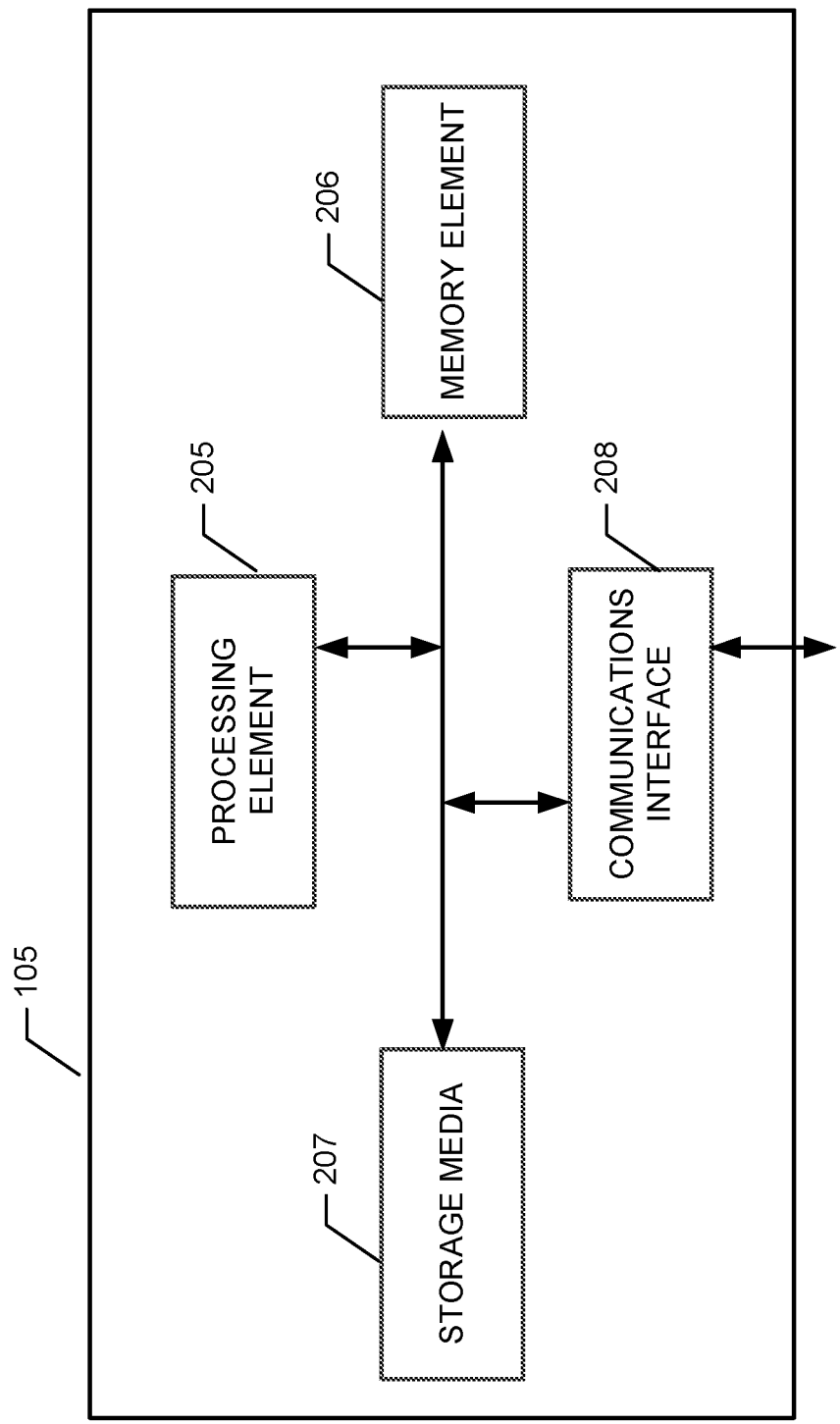
FIG. 2 is an example schematic illustration of an example feature representation computing entity in accordance with various embodiments of the present disclosure.

FIG. 2 provides a schematic of a feature representation computing entity 105 according to one embodiment of the present disclosure. In general, the terms computing entity, entity, device, system, and/or similar words used herein interchangeably may refer to, for example, one or more computers, computing entities, desktop computers, mobile phones, tablets, phablets, notebooks, laptops, distributed systems, items/devices, terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Such functions, operations, and/or processes may include, for example, transmitting, receiving, operating on, processing, displaying, storing, determining, creating/generating, monitoring, evaluating, comparing, and/or similar terms used herein. In one embodiment, these functions, operations, and/or processes can be performed on data, content, information, and/or similar terms used herein.

As indicated, in one embodiment, the feature representation computing entity 105 may also include one or more network and/or communications interfaces 208 for communicating with various computing entities, such as by communicating data, content, information, and/or similar terms used herein that can be transmitted, received, operated on, processed, displayed, stored, and/or the like. For instance, the feature representation computing entity 105 may communicate with other feature representation computing entities 105, one or more user computing entities 101A-101N, and/or the like.

As shown in FIG. 2, in one embodiment, the feature representation computing entity 105 may include or be in communication with a processing element 205 or more than one processing elements (also referred to as processors, processing circuitry, and/or similar terms used herein interchangeably) that communicate with other elements within the feature representation computing entity 105 via a bus, for example, or network connection. As will be understood, the processing element 205 may be embodied in a number of different ways. For example, the processing element 205 may be embodied as one or more complex programmable logic devices (CPLDs), microprocessors, multi-core processors, coprocessing entities, application-specific instruction-set processors (ASIPs), and/or controllers. Further, the processing element 205 may be embodied as one or more other processing devices or circuitry. The term circuitry may refer to an entirely hardware embodiment or a combination of hardware and computer program products. Thus, the processing element 205 may be embodied as integrated circuits, application specific integrated circuits (ASICs), field programmable gate arrays (FPGAs), programmable logic arrays (PLAs), hardware accelerators, other circuitry, and/or the like. As will therefore be understood, the processing element 205 may be configured for a particular use or configured to execute instructions stored in volatile or non-volatile media or otherwise accessible to the processing element 205. As such, whether configured by hardware or computer program products, or by a combination thereof, the processing element 205 may be capable of performing steps or operations according to embodiments of the present disclosure when configured accordingly.

In one embodiment, the feature representation computing entity 105 may further include or be in communication with volatile media (also referred to as volatile storage, memory, memory storage, memory circuitry and/or similar terms used herein interchangeably). In one embodiment, the volatile storage or memory may also include one or more memory element 206 as described above, such as RAM, DRAM, SRAM, FPM DRAM, EDO DRAM, SDRAM, DDR SDRAM, DDR2 SDRAM, DDR3 SDRAM, RDRAM, RIMM, DIMM, SIMM, VRAM, cache memory, register memory, and/or the like. As will be recognized, the volatile storage or memory element 206 may be used to store at least portions of the databases, database instances, database management system entities, data, applications, programs, program modules, scripts, source code, object code, byte code, compiled code, interpreted code, machine code, executable instructions, and/or the like being executed by, for example, the processing element 205 as shown in FIG. 2 and/or the processing element 308 as described in connection with FIG. 3. Thus, the databases, database instances, database management system entities, data, applications, programs, program modules, scripts, source code, object code, byte code, compiled code, interpreted code, machine code, executable instructions, and/or the like may be used to control certain aspects of the operation of the feature representation computing entity 105 with the assistance of the processing element 205 and operating system.

In one embodiment, the feature representation computing entity 105 may further include or be in communication with non-volatile media (also referred to as non-volatile storage, memory, memory storage, memory circuitry and/or similar terms used herein interchangeably). In one embodiment, the non-volatile storage or memory may include one or more non-volatile storage or storage media 207 as described above, such as hard disks, ROM, PROM, EPROM, EEPROM, flash memory, MMCs, SD memory cards, Memory Sticks, CBRAM, PRAM, FeRAM, RRAM, SONOS, racetrack memory, and/or the like. As will be recognized, the non-volatile storage or storage media 207 may store databases, database instances, database management system entities, data, applications, programs, program modules, scripts, source code, object code, byte code, compiled code, interpreted code, machine code, executable instructions, and/or the like. The term database, database instance, database management system entity, and/or similar terms used herein interchangeably and in a general sense to refer to a structured or unstructured collection of information/data that is stored in a computer-readable storage medium.

Storage media 207 may also be embodied as a data storage device or devices, as a separate database server or servers, or as a combination of data storage devices and separate database servers. Further, in some embodiments, storage media 207 may be embodied as a distributed repository such that some of the stored information/data is stored centrally in a location within the system and other information/data is stored in one or more remote locations. Alternatively, in some embodiments, the distributed repository may be distributed over a plurality of remote storage locations only. An example of the embodiments contemplated herein would include a cloud data storage system maintained by a third-party provider and where some or all of the information/data required for the operation of the recovery prediction system may be stored. Further, the information/data required for the operation of the recovery prediction system may also be partially stored in the cloud data storage system and partially stored in a locally maintained data storage system. More specifically, storage media 207 may encompass one or more data stores configured to store information/data usable in certain embodiments.

As indicated, in one embodiment, the feature representation computing entity 105 may also include one or more network and/or communications interfaces 208 for communicating with various computing entities, such as by communicating data, content, information, and/or similar terms used herein interchangeably that can be transmitted, received, operated on, processed, displayed, stored, and/or the like. For instance, the feature representation computing entity 105 may communicate with computing entities or communication interfaces of other feature representation computing entities 105, user computing entities 101A-101N, and/or the like.

As indicated, in one embodiment, the feature representation computing entity 105 may also include one or more network and/or communications interfaces 208 for communicating with various computing entities, such as by communicating data, content, information, and/or similar terms used herein interchangeably that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the feature representation computing entity 105 may be configured to communicate via wireless external communication networks using any of a variety of protocols, such as general packet radio service (GPRS), Universal Mobile Telecommunications System (UMTS), Code Division Multiple Access 2000 (CDMA2000), CDMA2000 1× (1×RTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), Institute of Electrical and Electronics Engineers (IEEE) 802.11 (Wi-Fi), Wi-Fi Direct, 802.16 (WiMAX), ultra-wideband (UWB), infrared (IR) protocols, near field communication (NFC) protocols, Wibree, Bluetooth protocols, wireless universal serial bus (USB) protocols, and/or any other wireless protocol. The feature representation computing entity 105 may use such protocols and standards to communicate using Border Gateway Protocol (BGP), Dynamic Host Configuration Protocol (DHCP), Domain Name System (DNS), File Transfer Protocol (FTP), Hypertext Transfer Protocol (HTTP), HTTP over TLS/SSL/Secure, Internet Message Access Protocol (IMAP), Network Time Protocol (NTP), Simple Mail Transfer Protocol (SMTP), Telnet, Transport Layer Security (TLS), Secure Sockets Layer (SSL), Internet Protocol (IP), Transmission Control Protocol (TCP), User Datagram Protocol (UDP), Datagram Congestion Control Protocol (DCCP), Stream Control Transmission Protocol (SCTP), HyperText Markup Language (HTML), and/or the like.

As will be appreciated, one or more of the feature representation computing entity's components may be located remotely from other feature representation computing entity 105 components, such as in a distributed system. Furthermore, one or more of the components may be aggregated and additional components performing functions described herein may be included in the feature representation computing entity 105. Thus, the feature representation computing entity 105 can be adapted to accommodate a variety of needs and circumstances.

b. Exemplary User Computing Entity

Figure 3:
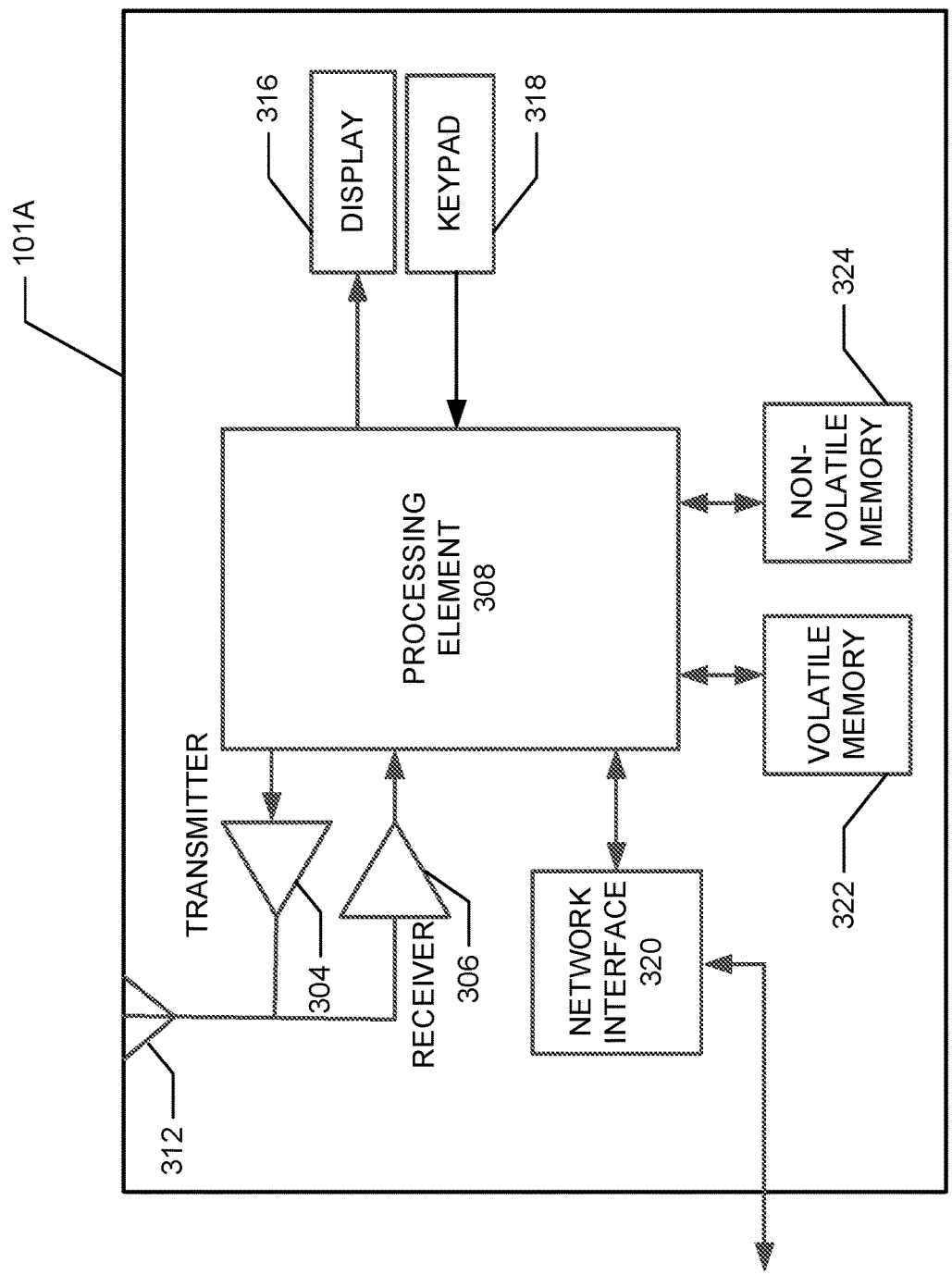
FIG. 3 is an example schematic illustration of an example user computing entity in accordance with various embodiments of the present disclosure.

FIG. 3 provides an illustrative schematic representation of one of the user computing entities 101A to 101N that can be used in conjunction with embodiments of the present disclosure. As will be recognized, the user computing entity may be operated by an agent and include components and features similar to those described in conjunction with the feature representation computing entity 105. Further, as shown in FIG. 3, the user computing entity may include additional components and features. For example, the user computing entity 101A can include an antenna 312, a transmitter 304 (e.g., radio), a receiver 306 (e.g., radio), and a processing element 308 that provides signals to and receives signals from the transmitter 304 and receiver 306, respectively. The signals provided to and received from the transmitter 304 and the receiver 306, respectively, may include signaling information/data in accordance with an air interface standard of applicable wireless systems to communicate with various entities, such as a feature representation computing entity 105, another user computing entity 101A, and/or the like. In this regard, the user computing entity 101A may be capable of operating with one or more air interface standards, communication protocols, modulation types, and access types. More particularly, the user computing entity 101A may comprise a network interface 320, and may operate in accordance with any of a number of wireless communication standards and protocols. In a particular embodiment, the user computing entity 101A may operate in accordance with multiple wireless communication standards and protocols, such as GPRS, UMTS, CDMA2000, 1×RTT, WCDMA, TD-SCDMA, LTE, E-UTRAN, EVDO, HSPA, HSDPA, Wi-Fi, WiMAX, UWB, IR protocols, Bluetooth protocols, USB protocols, and/or any other wireless protocol.

Via these communication standards and protocols, the user computing entity 101A can communicate with various other entities using Unstructured Supplementary Service data (USSD), Short Message Service (SMS), Multimedia Messaging Service (MMS), Dual-Tone Multi-Frequency (DTMF) Signaling, Subscriber Identity Module Dialer (SIM dialer), and/or the like. The user computing entity 101A can also download changes, add-ons, and updates, for instance, to its firmware, software (e.g., including executable instructions, applications, program modules), and operating system.

According to one embodiment, the user computing entity 101A may include location determining aspects, devices, modules, functionalities, and/or similar words used herein interchangeably. For example, the user computing entity 101A may include outdoor positioning aspects, such as a location module adapted to acquire, for example, latitude, longitude, altitude, geocode, course, direction, heading, speed, UTC, date, and/or various other information/data. In one embodiment, the location module can acquire data, sometimes known as ephemeris data, by identifying the number of satellites in view and the relative positions of those satellites. The satellites may be a variety of different satellites, including Low Earth Orbit (LEO) satellite systems, Department of Defense (DOD) satellite systems, the European Union Galileo positioning systems, the Chinese Compass navigation systems, Indian Regional Navigational satellite systems, and/or the like. Alternatively, the location information/data/data may be determined by triangulating the position in connection with a variety of other systems, including cellular towers, Wi-Fi access points, and/or the like. Similarly, the user computing entity 101A may include indoor positioning aspects, such as a location module adapted to acquire, for example, latitude, longitude, altitude, geocode, course, direction, heading, speed, time, date, and/or various other information/data. Some of the indoor aspects may use various position or location technologies including radio-frequency identification (RFID) tags, indoor beacons or transmitters, Wi-Fi access points, cellular towers, nearby computing devices (e.g., smartphones, laptops) and/or the like. For instance, such technologies may include iBeacons, Gimbal proximity beacons, Bluetooth Low Energy (BLE) transmitters, Near Field Communication (NFC) transmitters, and/or the like. These indoor positioning aspects can be used in a variety of settings to determine the location of someone or something to within inches or centimeters.

The user computing entity 101A may also comprise a user interface comprising one or more user input/output interfaces (e.g., a display 316 and/or speaker/speaker driver coupled to a processing element 308 and a touch screen, keyboard, mouse, and/or microphone coupled to a processing element 308). For example, the user output interface may be configured to provide an application, browser, user interface, dashboard, webpage, and/or similar words used herein interchangeably executing on and/or accessible via the user computing entity 101A to cause display or audible presentation of information/data and for user interaction therewith via one or more user input interfaces. The user output interface may be updated dynamically from communication with the feature representation computing entity 105. The user input interface can comprise any of a number of devices allowing the user computing entity 101A to receive data, such as a keypad 318 (hard or soft), a touch display, voice/speech or motion interfaces, scanners, readers, or other input device. In embodiments including a keypad 318, the keypad 318 can include (or cause display of) the conventional numeric (0-9) and related keys (#, *), and other keys used for operating the user computing entity 101A and may include a full set of alphabetic keys or set of keys that may be activated to provide a full set of alphanumeric keys. In addition to providing input, the user input interface can be used, for example, to activate or deactivate certain functions, such as screen savers and/or sleep modes. Through such inputs the user computing entity 101A can collect information/data, user interaction/input, and/or the like.

The user computing entity 101A can also include volatile storage or memory 322 and/or non-volatile storage or memory 324, which can be embedded and/or may be removable. For example, the non-volatile memory may be ROM, PROM, EPROM, EEPROM, flash memory, MMCs, SD memory cards, Memory Sticks, CBRAM, PRAM, FeRAM, RRAM, SONOS, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, RIMM, DIMM, SIMM, VRAM, cache memory, register memory, and/or the like. The volatile and non-volatile storage or memory can store databases, database instances, database management system entities, data, applications, programs, program modules, scripts, source code, object code, byte code, compiled code, interpreted code, machine code, executable instructions, and/or the like to implement the functions of the user computing entities 101A-101N.

c. Exemplary Networks

In one embodiment, the networks 103 may include, but are not limited to, any one or a combination of different types of suitable communications networks such as, for example, cable networks, public networks (e.g., the Internet), private networks (e.g., frame-relay networks), wireless networks, cellular networks, telephone networks (e.g., a public switched telephone network), or any other suitable private and/or public networks. Further, the networks 103 may have any suitable communication range associated therewith and may include, for example, global networks (e.g., the Internet), MANs, WANs, LANs, or PANs. In addition, the networks 103 may include medium over which network traffic may be carried including, but not limited to, coaxial cable, twisted-pair wire, optical fiber, a hybrid fiber coaxial (HFC) medium, microwave terrestrial transceivers, radio frequency communication mediums, satellite communication mediums, or any combination thereof, as well as a variety of network devices and computing platforms/systems provided by network providers or other entities.

Further, the networks 103 may utilize a variety of networking protocols including, but not limited to, TCP/IP based networking protocols. In some embodiments, the protocol is a custom protocol of JavaScript Object Notation (JSON) objects sent via a Websocket channel. In some embodiments, the protocol is JSON over RPC, JSON over REST/HTTP, and/or the like.

III. EXEMPLARY OPERATION

With reference to FIGS. 4, 5, 6, 7, 8, 9, 10, 11, 12, and 13, example steps, processes, procedures, operations, and/or the like associated with a feature representation generating platform/system in accordance with various embodiments of the present disclosure will be described.

While example embodiments of the present disclosure may be described in the context of generating feature representations for medical codes, as will be recognized, embodiments of the present invention are not limited to this context only.

a. Exemplary Feature Representations Generation

In the present disclosure, the term "feature" refers a property, characteristic, or variable associated with data and/or information. For example, features in the context of healthcare insurance claim processing may be medical codes associated with the medical claims.

In the present disclosure, the term "medical claim" refers to a request for payment that may be submitted to a health insurance provider for diagnosis, procedures, and/or services provided to a patient by a healthcare provider. In the present disclosure, the term "medical code" refers to an alphabetic, numeric, or alphanumeric code that may group, classify, and/or categorize healthcare diagnosis, procedures, and/or services. A medical code may be structured in accordance with a coding system, which may define the format and/or structure for the medical code (for example, defining the meaning of each letter/digit in a medical code). Example coding systems may include, but not limited to, Current Procedural Terminology (CPT), International Classification of Diseases, Tenth Revision, Procedure Coding System (ICD10PCS), International Classification of Diseases, Tenth Revision, Clinical Modification (ICD10CM), Systematized Nomenclature of Medicine (SNOMED), and Systematized Nomenclature of Medicine Clinical Terms, United States Edition (SNOMEDCT_US).

As an example, the medical code "OBYKOZO" in the coding system ICD10PCS describes the medical procedure of "transplantation of right lung, allogeneic, open approach." The medical code "OBYKOZO" is a child code of the medical code "0BYK" in the coding system ICD10PCS, which describes the medical procedure of "medical and surgical @ respiratory system @ transplantation @ lung, right." As shown in this example, medical codes may be considered as "categorical features," as they may represent label values (for example, descriptions of medical procedures associated with medical codes).

As described above, prediction models may be implemented to analyze data related to medical claims, and categorical features (such as medical codes) may not be recognizable or compatible input for prediction models. Therefore, categorical features (such as medical codes) may need to be transformed and/or converted to feature representations that are recognizable and compatible with the prediction models (such as feature vectors).

In the present disclosure, the term "feature representation" refers to structure, form, and/or format in which a feature is processed, stored, and/or transmitted within and/or between computing entities. The term "feature vector" refers to a type of feature representation that may include one or more numeric representations. For example, a feature vector of "n dimension" refers to an ordered collection having a number n of numeric representations. The term "feature space" refers to a collection of feature vectors that may be visualized in a two-dimension (2D) space, a three-dimension (3D) space, . . . or a n-dimension (nD) space. A feature space may comprise a plurality of nodes, and each of the plurality of nodes may be associated with a feature that is represented by a corresponding feature vector.

Figure 4:
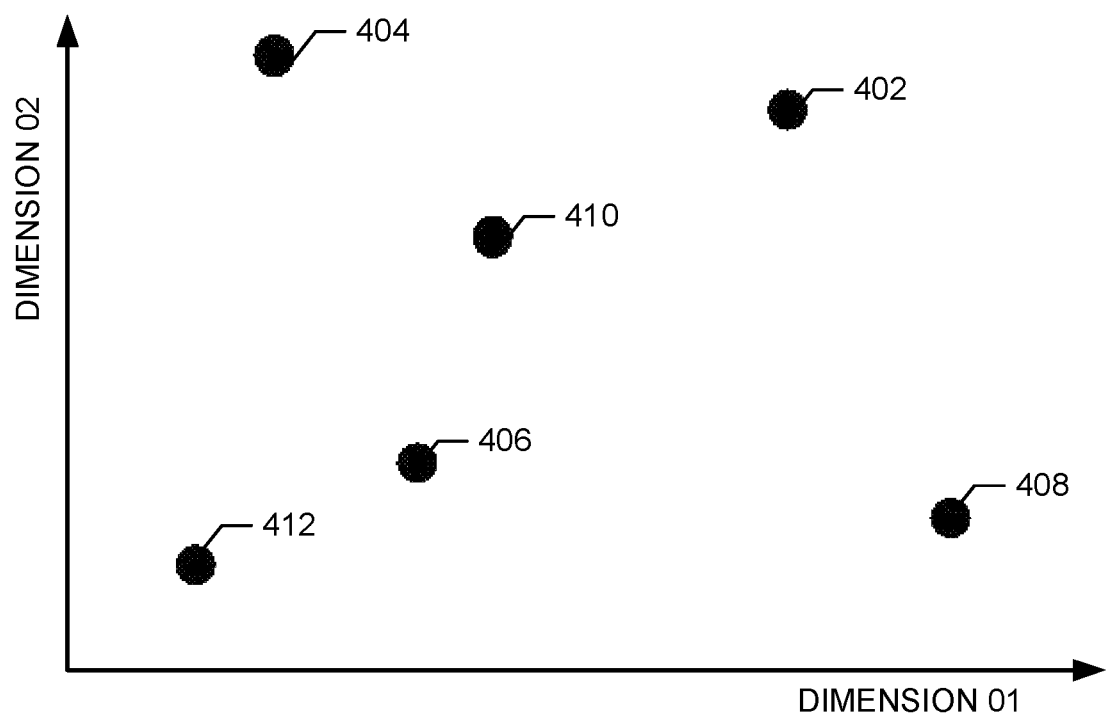
FIG. 4 and FIG. 5 illustrate example feature spaces in accordance with various embodiments of the present disclosure.
Figure 5:
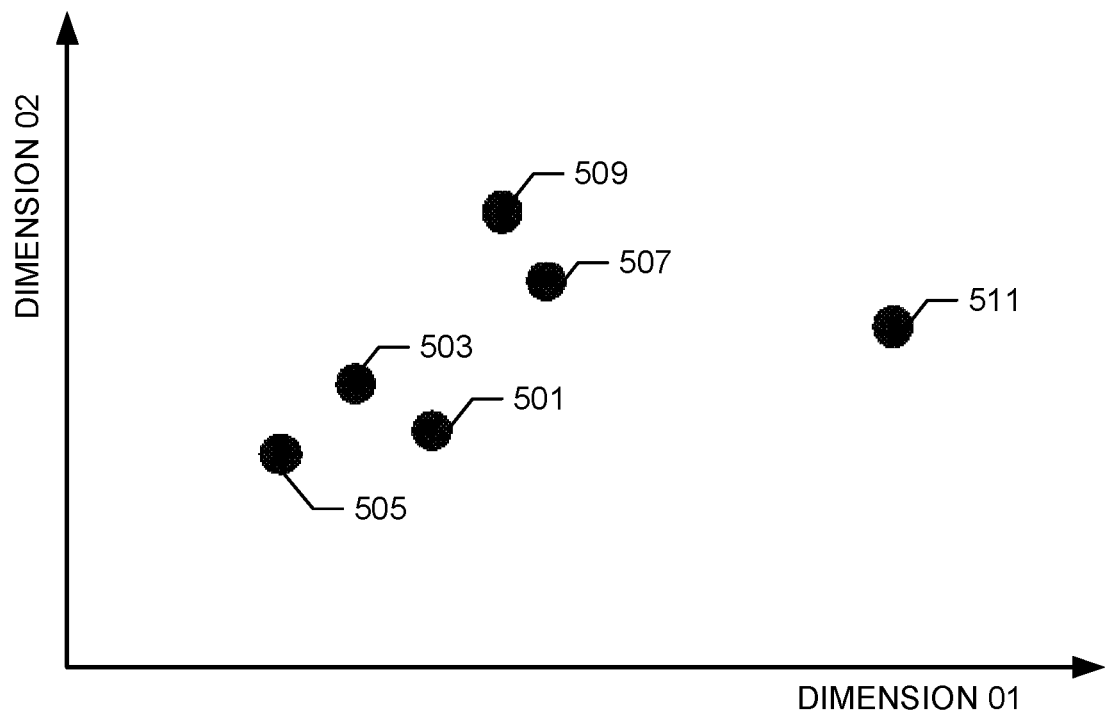

Referring now to FIG. 4 and FIG. 5, example feature spaces are illustrated. In particular, FIG. 4 illustrates an example feature space based on an example encoding technique for converting categorical features to features vectors, and FIG. 5 illustrates an example feature space based on an example embedding technique for converting categorical features to feature vectors.

In the example shown in FIG. 4, an example encoding technique is implemented on example categorical features in the form of city names (Rome, Paris, Dublin, Moscow, St. Petersburgh, N.Y.). The example encoding technique may encode and transform each city name into a feature vector. For example, the following example feature vectors may generated by the example encoding technique based on the city names Rome, Paris, Dublin, Moscow, St. Petersburgh, N.Y.:

| | | |
|---|---|---|
| Rome | = | [1, 0, 0, 0, 0, 0] |
| Paris | = | [0, 1, 0, 0, 0, 0] |
| Dublin | = | [0, 0, 1, 0, 0, 0] |
| Moscow | = | [0, 0, 0, 1, 0, 0] |
| St. Petersburg | = | [0, 0, 0, 0, 1, 0] |
| New York | = | [0, 0, 0, 0, 0, 1] |

In some examples, the number of numeric representations in each feature vector may correspond to the number of categories associated with the categorical features. As shown in the above example, there are six numeric representations in each feature vector, which correspond to six different categories (i.e. six different city names).

In some examples, each numeric representation in the feature vector may have a true ("1") or false ("0") value that indicates whether the categorical feature falls into a given category. As shown in the above example, the first numeric representation may indicate whether the corresponding city name falls into the category of "Rome." The second numeric representation may indicate whether the corresponding city name falls into the category of "Paris." The third numeric representation may indicate whether the corresponding city name falls into the category of "Dublin." The fourth numeric representation may indicate whether the corresponding city name falls into the category of "Moscow." The fifth numeric representation may indicate whether the corresponding city name falls into the category of "St. Petersburg." The sixth numeric representation may indicate whether the corresponding city name falls into the category of "New York."

In some examples, the feature vectors may be projected into a feature space. As mentioned above, the feature space may comprise a plurality of nodes, and each of the plurality of nodes may be associated with a categorical feature that is represented by a corresponding feature vector. In the example as shown in FIG. 4, node 402 represents Rome. Node 404 represents Paris. Node 406 represents Dublin. Node 408 represents Moscow. Node 410 represents St. Petersburgh. Node 412 represents New York.

Encoding techniques may be straightforward to apply (e.g. they do not require model training). However, encoding techniques may not maintain semantic information of categorical features, and, as a result, similar categorical features may not be placed close to each other in the feature space generated by encoding techniques. In the example described above, semantic information of the city names (such as information that two cities are in the same country) are not reflected in the feature vectors or in the feature space. For example, the feature vectors illustrated above are sparse and lengthy, as the numeric representations are all zeros except one. In the feature space as illustrated in FIG. 4, the node 410 (which presents St. Petersburgh) is placed further away from the node 408 (which represents Moscow) than from the node 406 (which represents Dublin), and therefore the feature space does not reflect the semantic information of the city names.

Referring now to FIG. 5, an example embedding technique is implemented on example categorical features in the form of city names (Rome, Paris, Dublin, Moscow, St. Petersburgh, N.Y.). The example embedding technique may embed and transform each city name into a feature vector. For example, the following example feature vectors may be generated by the example embedding technique based on the city names Rome, Paris, Dublin, Moscow, St. Petersburgh, N.Y.:

| | | |
|---|---|---|
| Rome | = | [0.50, 0.20, 0.11, 0.17, 0.10, 0.03] |
| Paris | = | [0.55, 0.18, 0.11, 0.19, 0.15, 0.08] |
| Dublin | = | [0.48, 0.51, 0.13, 0.17, 0.28, 0.02] |
| Moscow | = | [0.30, 0.15, 0.25, 0.65, 0.55, 0.10] |
| St. Petersburg | = | [0.20, 0.18, 0.32, 0.60, 0.80, 0.10] |
| New York | = | [0.01, 0.92, 0.51, 0.80, 0.12, 0.85] |

In some examples, the number of numeric representations in each feature vector may correspond to the number of categories associated with the categorical features, similar to those described above. As shown in the above example, there are six numeric representations in each feature vector, which correspond to six different categories (i.e. six different city names).

In some examples, each numeric representation in the feature vector may represent the similarity level between the categorical feature and a corresponding category. As shown in the above example, the first numeric representation may indicate the similarity level between the corresponding city name and the category of "Rome." The second numeric representation may indicate the similarity level between the corresponding city name and the category of "Paris." The third numeric representation may indicate the similarity level between the corresponding city name and the category of "Dublin." The fourth numeric representation may indicate the similarity level between the corresponding city name and the category of "Moscow." The fifth numeric representation may indicate the similarity level between the corresponding city name and the category of "St. Petersburg." The sixth numeric representation may indicate the similarity level between the corresponding city name and the category of "New York."

In some examples, the feature vectors may be projected into a feature space. As mentioned above, the feature space may comprise a plurality of nodes, and each of the plurality of nodes may be associated with a categorical feature that is represented by a corresponding feature vector. In the example as shown in FIG. 5, node 501 represents Rome. Node 503 represents Paris. Node 505 represents Dublin. Node 507 represents Moscow. Node 509 represents St. Petersburgh. Node 511 represents New York.

Embedding techniques may capture the semantic information of features and compress the information into a predefined feature vector. As illustrated in the example above, embedding techniques may transform categorical features into meaningful numeric representations, and may preserve the information of similarity/neighborhood associated with the features. For example, the node 509 (which presents St. Petersburg) is placed close to the node 507 (which represents Moscow). However, embedding techniques do not capture the structural information (including global relation and local relations) between different features. For example, the example feature space shown in FIG. 5 does not capture the hierarchical relationship between Moscow and St. Petersburg (e.g. capital city and non-capital city).

Various examples of the present disclosure may overcome challenges, deficiencies and problems associated with encoding techniques and embedding techniques. For example, examples of the present disclosure may capture both the semantic information and the structural information of categorical features (for example, medical codes), may generalize any categorical features used in any dataset (for example, may extend to unseen or new medical codes), and may not be prone to problems such as sparsity described above. As such, when various examples of the present disclosure are implemented to transfer categorical features (for example, medical codes) into feature vectors (which may include numeric representations), the feature vectors may be provided to prediction models as input data, and the prediction models may generate predictions that have a higher accuracy, better receiver operating characteristic (ROC) and/or lower false positive rate.

Figure 6:
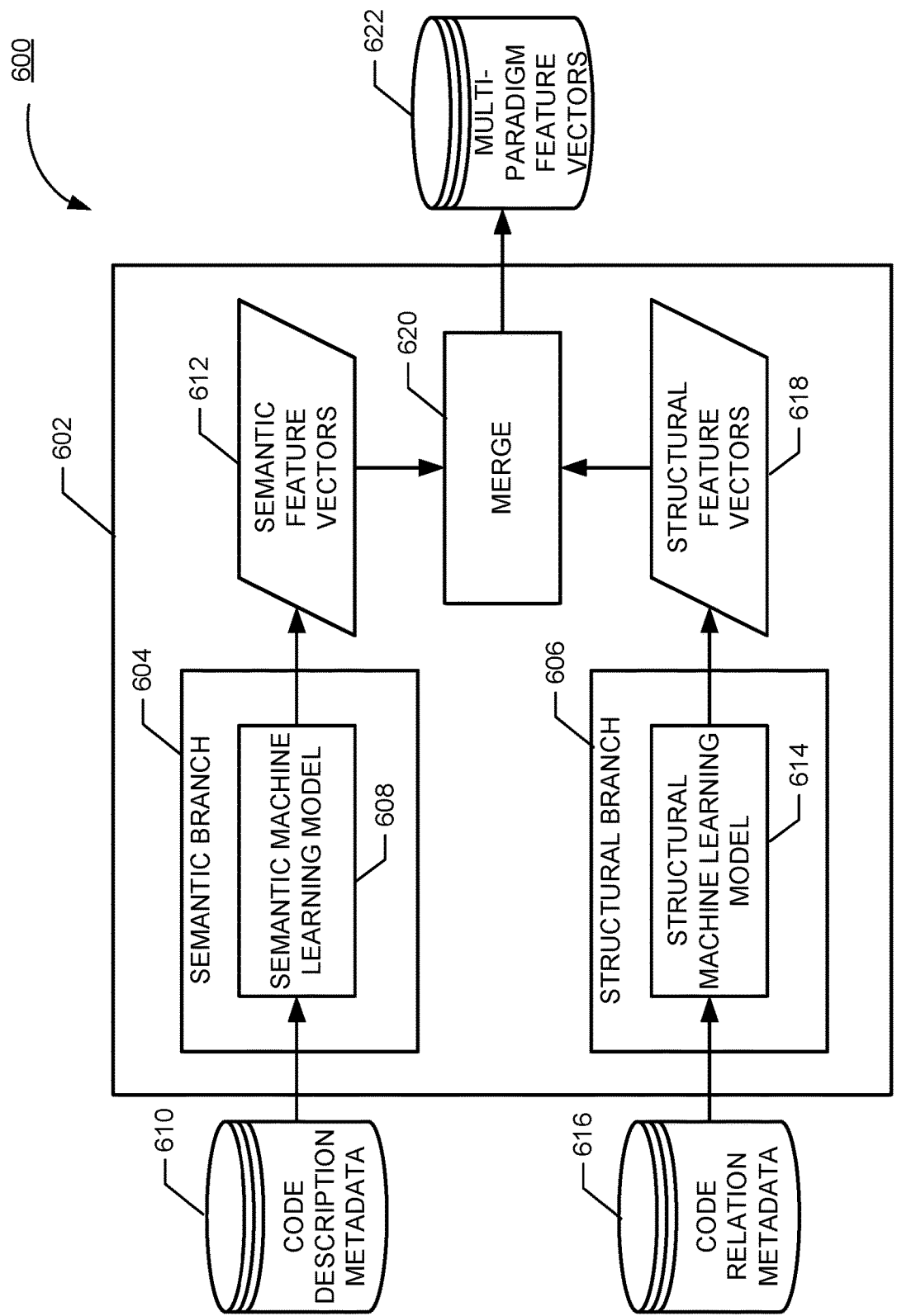
FIG. 6 is an example schematic architecture illustration associated with an example feature representation generating platform/system in accordance with various embodiments of the present disclosure.

Referring now to FIG. 6, an example schematic architecture 600 associated with an example feature representation generating platform/system in accordance with various embodiments of the present disclosure is shown.

In the example shown in FIG. 6, the example schematic architecture 600 may comprise a feature representation generating component 602. The feature representation generating component 602 may be implemented in the form of a computer program product, an entirely hardware embodiment, or a combination of hardware and computer program products. For example, the feature representation generating component 602 may be implemented as a software component that is stored in a computer-readable storage medium (for example, the memory element 206 or the storage media 207 of the feature representation computing entity 105 described above in connection with FIG. 1 and FIG. 2).

In the example shown in FIG. 6, the feature representation generating component 602 may comprise two branches: a semantic branch 604 and a structural branch 606.

In some examples, the semantic branch 604 may comprise a semantic machine learning model 608. In the present disclosure, the term "semantic machine learning model" refers to a computer algorithm that is configured to analyze and/or extract semantic information associated with data. The semantic machine learning model 608 may receive code description metadata 610 associated with a plurality of codes as input, which may comprise a textual description of the code. The semantic machine learning model 608 may generate a plurality of semantic feature vectors 612 for the plurality of codes based on the code description metadata 610. The plurality of semantic feature vectors 612 may represent semantic information associated with the plurality of codes. For example, the plurality of semantic feature vectors 612 may comprise a semantic feature vector for each code of the plurality of codes, and each semantic feature vector that is associated with a code comprises numeric representations of one or more phrases used in the textual description for the code. Additional details of the code description metadata 610, the semantic machine learning model 608, and the plurality of semantic feature vectors 612 are described herein.

In some examples, the structural branch 606 may comprise a structural machine learning model 614. In the present disclosure, the term "structural machine learning model" refers to a computer algorithm that is configured to analyze and/or extract structural information associated with data. The structural machine learning model 614 may receive code relation metadata 616 associated with a plurality of codes as input, which may describe one or more relationships between the plurality of codes. The structural machine learning model 614 may generate a plurality of structural feature vectors 618 for the plurality of codes based on the code relation metadata 616. The plurality of structural feature vectors 618 may represent local and global connections between the plurality of codes according to the relationships between the plurality of codes. For example, the plurality of structural feature vectors 618 may reflect similarities and hierarchies of the plurality of codes. Additional details of the code relation metadata 616, the structural machine learning model 614, and the plurality of structural feature vectors 618 are described herein.

In some examples, the feature representation generating component 602 may merge the plurality of semantic feature vectors 612 and the plurality of structural feature vectors 618 at operation 620 to generate a plurality of multi-paradigm feature vectors 622. In the present disclosure, the term "multi-paradigm feature vector" refer to a feature vector that may not only capture semantic information associated with the feature, but also structural information between the feature and other features in a dataset. In some examples, the feature representation generating component 602 may store the multi-paradigm feature vectors 622 in a data storage device. Subsequently, the multi-paradigm feature vectors 622 may be provided as input to machine learning models (for example, prediction models).

In some examples, subsequently, the multi-paradigm feature vectors 622 may be provided as input to machine learning models (for example, clustering or prediction models) or to other purposes (for example, visualization) or to other downstream tasks. Additionally, or alternatively, other applications and/or use cases may be implemented based on examples of the present disclosure.

While the example shown in FIG. 6 illustrates two branches (i.e. the semantic branch 604 and the structural branch 606), it is noted that the scope of the present disclosure is not limited to these two branches only. For example, more than two branches may be implemented (for example, other branches may be added to capture different characteristics of input/external data with heterogeneous format (e.g. images)).

Referring now to FIG. 7, an example method 700 illustrates example operations of generating feature representations in accordance with embodiments of the present disclosure.

The example method 700 may start at step/operation 701. At step/operation 703, a computing entity (such as the feature representation computing entity 105 described above in connection with FIG. 1 and FIG. 2) may include means (such as the processing element 205 of the feature representation computing entity 105 described above in connection with FIG. 2) for generating a dataset.

In some examples, the dataset may represent raw data that may need to be transformed into feature representations that are recognizable and compatible as input for a prediction model. For example, the dataset may comprise categorical features that may need to be transformed into feature vectors, as described above.

In some examples, the dataset generated at step/operation 703 may be in the form of a code dataset that comprises a plurality of codes. For example, the plurality of codes may be associated with a plurality of medical codes.

In some examples, the plurality of codes may be associated with the same predictive entity. In the present disclosure, the term "predictive entity" refers to a subject matter for which a computer program algorithm or a machine learning model (for example, a prediction model) is configured to generate, determine and/or recognize a prediction, an estimate, a pattern, and/or the like. As an example, the predictive entity may be a medical claim for which the prediction model is configured to predict whether there is healthcare fraud, waste, abuse, and error associated with the medical claim.

In some examples, the plurality of medical codes in the code dataset may be associated with a same coding system. Continuing from the medical code example above, the plurality of medical codes may be formatted in accordance with the coding system ICD10PCS described above.

In some examples, the plurality of medical codes in the code dataset may be associated with different coding systems. Continuing from the medical code example above, a first portion of the plurality of medical codes may be associated with a first coding system, and a second portion of the plurality of medical codes may be associated with a second coding system different from the first coding system. For example, the first portion of the plurality of medical codes may be formatted in accordance with the coding system ICD10PCS described above, and the second portion of the plurality of medical codes may be formatted in accordance with the coding system SNOMEDCT_US described above.

In some examples, the plurality of codes in the code dataset may be associated with code description metadata and code relation metadata. In some examples, the code description metadata may comprise textual descriptions associated with the plurality of codes in the code dataset. In some examples, the code relation metadata may describe one or more relationships between the plurality of codes.

Continuing from the medical code example above, the computing entity may iterate through each code in plurality of medical codes, and retrieve metadata associated with each codes from, for example, a data storage device. For example, the computing entity may retrieve textual descriptions in English natural language (and/or other language(s) as well) associated with the medical codes as part of the code description metadata. As another example, the computing entity may retrieve one or more relationships between codes within a specific coding system and/or between different coding systems as part of the code relation metadata. Additional example details of the code description metadata and the code relation metadata are described further herein.

In some examples, the computing entity may provide code description metadata to a semantic branch (for example, the semantic branch 604 described above in connection with FIG. 6) that may comprise a semantic machine learning model (for example, the semantic machine learning model 608 described above in connection with FIG. 6). As described above, the code description metadata may comprise a textual description of the code. Example steps/operations associated with the semantic branch and the semantic machine learning model are described further herein.

In some examples, the computing entity may provide code relation metadata to a structural branch (for example, the structural branch 606 described above in connection with FIG. 6) that may comprise a structural machine learning model (for example, the structural machine learning model 614 described above in connection with FIG. 6). As described above, the code relation metadata may describe one or more relationships between the plurality of codes. Example steps/operations associated with the structural branch and the structural machine learning model are described further herein.

While the above description provides code dataset as an example, it is noted that the scope of the present disclosure is not limited to code dataset only. For example, at the step/operation 703, the computing entity may comprise means for generating a dataset that may comprise other form(s) of categorical features.

At step/operation 705, a computing entity (such as the feature representation computing entity 105 described above in connection with FIG. 1 and FIG. 2) may include means (such as the processing element 205 of the feature representation computing entity 105 described above in connection with FIG. 2) for generating a plurality of semantic feature vectors based at least in part on the code description metadata.

In some examples, the plurality of semantic feature vectors may be generated based at least in part on processing the code description metadata for each code of the plurality of codes using the semantic machine learning model. As described above, the computing entity may comprise means for providing the code description metadata as input to the semantic machine learning model.

In some examples, the semantic machine learning model may comprise at least one natural language processing (NLP) machine learning model. The NLP machine learning model may analyze, extract, and/or exploit textual description of the code description metadata, and may learn and/or generate a feature representation that may capture semantic information of codes (for example, codes that are described in a similar manner and/or with similar medical terminology). For example, the NLP machine learning model may learn the representation of each phrase within the textual description of the code description metadata (such as through an uni-gram model, a bi-gram model, a tri-gram model, a sub-gram model, and/or a n-gram model), and may successively learn the representation for an entire sentence within the textual description of the code description metadata.

In the present disclosure, the term "phrase" may refer to an "n-gram" that represents a contiguous sequence of n items from a text or speech, such as a word or a sentence associated with the description of the medical code. For example, the n-gram of size 1 is referred to as a "unigram." The n-gram of size 2 is referred to as a "bigram." The n-gram of size 3 is referred to as a "trigram." In some examples, the size of the n-gram (i.e. the value of n) may be defined by the semantic machine learning model. For example, the semantic machine learning model may define the value of n as a parameter, which may be acquired by the semantic machine learning model when generating the plurality of semantic feature vectors. In some examples, the semantic machine learning model may define the value of n as a hyperparameter, which may be provided to the semantic machine learning model (for example, a user may provide the value of n to the semantic machine learning model). In some examples, one or more other model(s), such as a sub-gram model (e.g. splitting one word into two or more subwords), may be implemented in examples of the present disclosure.

In some examples, the semantic machine learning model may be a Word2Vec model. In some examples, the semantic machine learning model may comprise a Word2Vec model and a Sentence2Vec model. While the above description uses the Word2Vec model and the Sentence2Vec model as examples, it is noted that the scope of the present disclosure is not limited to these models only. Additionally, or alternatively, other models and/or techniques may be implemented for the semantic machine learning model, including, but not limited to, generic language model(s) and/or natural language processing technique(s), FastText approach (based on subwords information), Bidirectional Encoder Representations from Transformers (BERT) model, Biomedical Bidirectional Encoder Representations from Transformers (BioBERT) model, and/or the like. Example details are described further herein.

In some examples, the semantic machine learning model may be trained on a data corpus to learn the semantic information associated with concepts and phrases. Continuing from the medical code example above, the semantic machine learning model may be trained to associate medical concepts with medical phrases, such that the semantic machine learning model may recognize same medical conditions but described with different terminologies in the textual description of the code description metadata. For example, the semantic machine learning model may be trained based on data from public medical ontologies (for example, Unified Medical Language System (UMLS)), which provides the leverage of a large medical database with complete codes, therefore enabling the semantic machine learning model to extract semantic information even if the dataset is associated with a rare medical case that is represented with a small dataset. In some examples, these models could be pre-trained additionally, or alternatively, on other larger corpora (e.g. not only on UMLS, but also on medical papers, medical clinical notes, medical books, etc., and/or also on corpora that is not limited to the medical domain).

In some examples, the plurality of semantic feature vectors may represent semantic information associated with data in the dataset generated at step/operation 703. In the present disclosure, the term "semantic information" refers to information related to the meaning and/or denotation of data. For example, semantic information may comprise information that indicate the similarities and/or differences associated with categorical features. Continuing from the medical code example above, semantic information may include information such as similarities and differences between diagnosis, procedures, and/or services that two medical codes represent.

In some examples, the plurality of semantic feature vectors may comprise a semantic feature vector for each code of the plurality of codes. In some examples, each semantic feature vector that is associated with a code may comprise numeric representations of one or more phrases used in the textual description for the code. Example details are described further herein.

At step/operation 707, a computing entity (such as the feature representation computing entity 105 described above in connection with FIG. 1 and FIG. 2) may include means (such as the processing element 205 of the feature representation computing entity 105 described above in connection with FIG. 2) for generating a plurality of structural feature vectors based at least in part on the code relation metadata.

In some examples, the plurality of structural feature vectors may be generated based at least in part on processing the code relation metadata using a structural machine learning model. As described above, the computing entity may comprise means for providing the code relation metadata as input to the structural machine learning model. In some examples, the structural machine learning model may comprise a graph machine learning model. In the present disclosure, the term "graph machine learning model" refers to a type of machine learning model that may analyze, extract, and/or exploit structural relationships between data points. For example, a graph machine learning model may analyze, extract, and/or exploit hierarchical relationships between codes, and may learn and/or generate a feature representation that may capture global and local relations for codes. Example graph machine learning model may include, but not limited to, knowledge graph models such as ComplEx, TransE, RotatE, LiteralE, or graph convolutional networks such as GCN, GraphSAGE, and/or the like. Additional details of structural machine learning model (and graph machine learning model) are described further herein.

In some examples, the structural machine learning model may be trained on a data corpus to learn the structural information associated with codes. Continuing from the medical code example above, the data corpus may comprise example connections, relations, and/or hierarchies among medical codes within the same coding system and/or between different coding systems. For example, the structural machine learning model may be trained based on data from public medical ontologies (for example, Unified Medical Language System (UMLS)), which provides the leverage of a large medical database with complete codes, therefore enabling the structural machine learning model to extract structural information even if the dataset is associated with a rare medical case that is represented with a small dataset.

In some examples, the plurality of structural feature vectors may represent structural information associated with data in the dataset generated at step/operation 703. In the present disclosure, the term "structural information" refers to information related to the connections, relations, and/or hierarchies of data. For example, structural information may comprise information that may indicate the parent/child relationship associated with categorical features. Continuing from the medical code example above, structural information may include information such as parentage of a medical code.

At step/operation 709, a computing entity (such as the feature representation computing entity 105 described above in connection with FIG. 1 and FIG. 2) may include means (such as the processing element 205 of the feature representation computing entity 105 described above in connection with FIG. 2) for generating a plurality of multi-paradigm feature vectors.

In some examples, the plurality of multi-paradigm feature vectors may be generated based at least in part on the plurality of semantic feature vectors (as described above in connection with step/operation 705) and the plurality of structural feature vectors (as described above in connection with step/operation 707). For example, the computing entity may comprise means for merging the plurality of semantic feature vectors and the plurality of structural feature vectors, and the resultant feature vectors from the merging are multi-paradigm feature vectors.

In some examples, one or more merging techniques associated with combining feature vectors may be implemented for merging the plurality of semantic feature vectors and the plurality of structural feature vectors. Example merging techniques may include, but not limited to concatenation, blending, and/or mathematical operations between feature vectors. For example, the computing entity may comprise means for concatenating the plurality of semantic feature vectors and the plurality of structural feature vectors, and for storing the concatenated feature vectors as multi-paradigm feature vectors. Additionally, or alternatively, other merging techniques may be implemented, including, but not limited to, machine learning models to combine the plurality of semantic feature vectors and the plurality of structural feature vectors.

As described above, the multi-paradigm feature vectors are drawn from both the semantic branch and the structural branch, and thus combine both semantic information and structural information associated with data in the dataset generated at step/operation 703.

At step/operation 711, a computing entity (such as the feature representation computing entity 105 described above in connection with FIG. 1 and FIG. 2) may include means (such as the processing element 205 of the feature representation computing entity 105 described above in connection with FIG. 2) for generating a prediction for the predictive entity by processing the plurality of multi-paradigm feature vectors using a prediction model.

In the present disclosure, the term "prediction" refers to an output of a computer algorithm (for example, a prediction model as defined herein) that may indicate the likelihood or probability of a particular outcome. The term "prediction model" refers to a computer algorithm that may generate a prediction based on, for example, implementing machine learning techniques and/or artificial intelligence techniques.

In some examples, the prediction model may be an unsupervised machine learning model. In the present disclosure, the term "unsupervised machine learning model" refers to a machine learning model that may identify trends and/or patterns in the data without the need for training using training data. For example, the computing entity may include means that processing the plurality of multi-paradigm feature vectors using an unsupervised machine learning model that is configured to detected fraud, waste, abuse, or error. In such an example, the unsupervised machine learning model may determine whether there is any anomalies associated with the predictive entity (for example, a medical claim), and may predict whether a medical claim is associated with suspected fraud, waste, abuse, or error. For example, based on determining that there is an anomaly, the unsupervised machine learning model may generate a prediction that the medical claim is associated with potential fraud, waste, abuse, or error. As another example, based on determining that there is no anomaly, the unsupervised machine learning model may generate a prediction that the medical claim is not associated with potential fraud, waste, abuse, or error.

In some examples, the prediction model may be a supervised machine learning model. In the present disclosure, the term "supervised machine learning model" refers to a machine learning model that may identify trends and/or patterns in the data based on example input-output pairs (i.e., training data). For example, the computing entity may include means that process the plurality of multi-paradigm feature vectors using a supervised machine learning model, and the supervised machine learning model may be trained based on the plurality of multi-paradigm feature vectors. In such an example, the supervised machine learning model may provide more accurate predictions of fraud, waste, abuse, or error as compared to other machine learning models that are not trained using multi-paradigm feature vectors in accordance with examples of the present disclosure.

At step/operation 713, a computing entity (such as the feature representation computing entity 105 described above in connection with FIG. 1 and FIG. 2) may include means (such as the processing element 205 of the feature representation computing entity 105 described above in connection with FIG. 2) for performing one or more prediction-based action(s) based on the prediction.

Continuing from the unsupervised machine learning model example above, the computing entity may comprise means that is configured to generate one or more warning messages when the prediction indicates that there is potential fraud, waste, abuse, or error associated with the medical claim. The warning messages may be rendered for display on a display of a user computing entity (for example, one of the user computing entities 101A, 101B, . . . 101N descried above in connection with FIG. 1 and FIG. 2), such that a user operating the user computing entity may take appreciate action(s) (for example, manually review the medical claim).

While the above examples describe example practical applications of multi-paradigm feature vectors in the context of medical fraud, waste, abuse, and error detection, it is noted that the scope of the present disclosure is not limited to implementing multi-paradigm feature vectors in this context only. Additionally, or alternatively, the multi-paradigm feature vectors may be implemented in other contexts, including, but not limited to, determining disease progressions. For example, the multi-paradigm feature vectors may be generated based on medical claims and/or medical codes as described above, and may be processed by a disease progression prediction model. The disease progression prediction model may generate a prediction that describes the time course of disease status and likely severity associated with the disease. Based on the prediction, the computing entity may comprise means that may generate one or more suggestions (for example, actions to take that may reduce the risk of disease progression).

The example method 700 may end at step/operation 715.

In various examples of the present disclosure, all information (including semantic information and structural information) related to example categorical features (such as medical codes) are present in the multi-paradigm feature representations (for example, multi-paradigm feature vectors). These feature representations may be easily fed and ingested by a machine learning model (such as a prediction model) to accomplish its required tasks (for example, prediction generation, data classification, regression analysis, etc.). As such, various examples of the present disclosure may enable machine learning models to receive semantic information and structural information of medical codes, and to decide which information is relevant to the task.

b. Exemplary Semantic Branch

As described above, the computing entity may provide code description metadata (for example, the code description metadata 610 described above in connection with FIG. 6) associated with a plurality of codes in the code dataset to a semantic branch (for example, the semantic branch 604 described above in connection with FIG. 6). The code description metadata may comprise textual descriptions associated with the plurality of codes.

As an example, TABLE 1 below illustrates example textual descriptions of example code description metadata associated with a plurality of example codes.

TABLE 1

Example Code Description Metadata

| Coding System | Code | Textual Description |
| --- | --- | --- |
| ICD10PCS | 0BYK | Medical and Surgical @ Respiratory System @ Transplantation @ Lung, Right |
| ICD10PCS | 0BYK0 | Medical and Surgical @ Respiratory System @ Transplantation @ Lung, Right @ Open |
| ICD10PCS | 0BYK0Z | Medical and Surgical @ Respiratory System @ Transplantation @ Lung, Right @ Open @ No Device |
| ICD10PCS | 0BYK0Z0 | Transplantation of Right Lung, Allogeneic, Open Approach |
| ICD10PCS | 0BYK0Z1 | Transplantation of Right Lung, Syngeneic, Open Approach |
| ICD10PCS | 0BYK0Z2 | Transplantation of Right Lung, Zooplastic, Open Approach |

In the example shown in TABLE 1 above, the plurality of example codes may be associated with a plurality of medical codes that are formatted in accordance with the same coding system (i.e. the coding system ICD10PCS). When generating the code dataset, the computing entity (such as the feature representation computing entity 105 described above in connection with FIG. 1 and FIG. 2) may include means (such as the processing element 205 of the feature representation computing entity 105 described above in connection with FIG. 2) for retrieving code description metadata associated with each medical code from one or more data storage devices (such as a data storage device that stores information related to medical codes of the coding system ICD10PCS), and for extracting textual descriptions associated with each medical code from the code description metadata.

In the example shown in TABLE 1 above, the textual descriptions may be in the form of English natural language (and/or other language(s) as well) that may describe a healthcare diagnosis, procedure, and/or service represented by a corresponding medical code. For example, the textual description for the code 0BYK may comprise "Medical and Surgical @ Respiratory System @ Transplantation @ Lung, Right," which may indicate that the code 0BYK describes a healthcare procedure that is medical and surgical in nature, and is associated with the respiratory system and transplantation of right lung.

While the examples illustrated in TABLE 1 comprise medical codes in accordance with the same coding system, as described above, the plurality of medical codes in the code dataset may be associated with different coding systems. As another example, TABLE 2 below illustrates example code description metadata associated with a plurality of codes in accordance with different coding systems.

TABLE 2

Example Code Description Metadata

| Coding System | Code | Textual Description |
| --- | --- | --- |
| ICD10PCS | I06PY4 | Medical and Surgical @ Lower Veins @ Removal @ Lower Vein @ Percutaneous Endoscopic |
| SNOMEDCT_US | 705741007 | Device associated with osteotomes (physical object) |
| ICD10PCS | B53HZZZ | Imaging @ Veins @ Magnetic Resonance Imaging (MRI) @ Pelvic (Iliac) Veins, Bilateral @ None @ None @ None |
| SNOMEDCT_US | 714456003 | Structure of muscle acting on joint of thumb (body structure) |
| SNOMEDCT_US | 53393007 | Bromine radioisotope (substance) |
| SNOMEDCT_US | 433873002 | Specimen from spermatic cord obtained by biopsy (specimen) |

In the example shown in TABLE 2 above, the plurality of example codes may be associated with a plurality of medical codes that are formatted in accordance with a variety of coding systems (i.e. the coding systems ICD10PCS and SNOMEDCT_US). When generating the code dataset, the computing entity (such as the feature representation computing entity 105 described above in connection with FIG. 1 and FIG. 2) may include means (such as the processing element 205 of the feature representation computing entity 105 described above in connection with FIG. 2) for retrieving code description metadata associated with each medical code from one or more data storage devices (such as one or more data storage devices that store information related to medical codes of the coding systems ICD10PCS and SNOMEDCT_US), and for extracting textual descriptions associated with each medical code from the code description metadata.

Similar to the example shown in TABLE 1, the textual descriptions shown in TABLE 2 may be in the form of English natural language (and/or other language(s) as well) that may describe a healthcare diagnosis, procedure, and/or service that a corresponding medical code may represent. For example, the textual description for the code 705741007 from the coding system SNOMEDCT_US may comprise "Device associated with osteotomes (physical object)," which may indicate that the code 705741007 describes a healthcare device associated with osteotomes.

As described above, the semantic branch may comprise a semantic machine learning model (for example, the semantic machine learning model 608 described above in connection with FIG. 6). The semantic machine learning model may generate a plurality of semantic feature vectors based on the code description metadata, and the plurality of semantic feature vectors may represent semantic information associated with codes. For example, the plurality of semantic feature vectors may comprise a semantic feature vector for each code of the plurality of codes, and each semantic feature vector that is associated with a code comprises numeric representations of one or more phrases used in the textual description for the code.

Referring now to FIG. 8, an example method 800 illustrates example operations of an example semantic branch in accordance with embodiments of the present disclosure.

The example method 800 may start at step/operation 802. At step/operation 804, a computing entity (such as the feature representation computing entity 105 described above in connection with FIG. 1 and FIG. 2) may include means (such as the processing element 205 of the feature representation computing entity 105 described above in connection with FIG. 2) for possessing the textual description of the code using a Word2Vec model.

As described above, the semantic machine learning model may comprise one or more computer algorithms that may analyze words and/or phrases within textual descriptions of code description metadata associated with the plurality of codes, and may identify similarities between these words and/or phrases.

For example, the semantic machine learning model may comprise a Word2Vec model. The Word2Vec model may comprise an artificial neural network that may comprise two (or more) layers of artificial neural nodes to provide word embedding. The Word2Vec model may be trained to identify and/or reconstruct linguistic contexts of words and/or phrases. In this example, the computing entity may provide each word or phrase in the textual description to the Word2Vec model, and the Word2Vec model may generate numeric representations of one or more words/phrases used in the textual description for the code. For example, the Word2Vec model may calculate a similarity level between words/phrases mathematically, and may group similar words or phrases together or place them close to one another in the feature space.

In some examples, the computing entity may comprise means for implementing transfer learning techniques. For example, the Word2Vec model may be trained on a large data corpus associated with medical codes in order to capture more relevant semantic information that may not be available in all textual descriptions associated with medical codes in the code dataset.

At step/operation 806, a computing entity (such as the feature representation computing entity 105 described above in connection with FIG. 1 and FIG. 2) may include means (such as the processing element 205 of the feature representation computing entity 105 described above in connection with FIG. 2) for possessing the textual description of the code using a Sentence2Vec model.

As described above, the semantic machine learning model may comprise one or more computer algorithms that may analyze sentences or phrases within textual descriptions of code description metadata associated with the plurality of codes, and may identify similarities between these sentences or phrases.

For example, the semantic machine learning model may comprise a Sentence2Vec model. The Sentence2Vec model may comprise an artificial neural network that may comprise two or more layers. The Sentence2Vec model may be trained to identify and/or reconstruct linguistic contexts of sentences or phrases. In this example, the computing entity may provide each sentence or phrase in the textual description to the Sentence2Vec model, and the Sentence2Vec model may generate numeric representations of one or more sentences/phrases used in the textual description. For example, the Sentence2Vec model may calculate a similarity level between sentences/phrases mathematically, and may group similar sentences or phrases together or place them close to one another in the feature space.

In some examples, the computing entity may comprise means for implementing transfer learning techniques. For example, the Sentence2Vec model may be trained on a large data corpus associated with medical codes in order to capture more relevant semantic information that may not be available in all textual descriptions associated with medical codes in the code dataset.

In some examples, the computing entity may include means for generating the plurality of semantic feature vectors based on the outcomes from the Word2Vec model and/or the Sentence2Vec model.

In some examples, the plurality of semantic feature vectors comprise a semantic feature vector for each code of the plurality of codes. For example, the computing entity may include means for calculating numeric representations of one or more phrases used in the textual description for each code (for example, based on the Word2Vec model and/or the Sentence2Vec model described above), and may generate a semantic feature vector for each code based on the corresponding numeric representations.

While the above description uses the Word2Vec model and the Sentence2Vec model as examples, it is noted that the scope of the present disclosure is not limited to these models only. For example, examples of present disclosure may implement only one of the Word2Vec model or the Sentence2Vec model in generating the semantic features vectors. Additionally, or alternatively, other models and/or techniques may be implemented for the semantic machine learning model, including, but not limited to, generic language model(s) and/or natural language processing technique(s), FastText approach (based on subwords information), Bidirectional Encoder Representations from Transformers (BERT) model, Biomedical Bidirectional Encoder Representations from Transformers (BioBERT) model, and/or the like.

The example method 800 may end at step/operation 808.

In some examples, the computing entity may comprise means for calculating a plurality of similarity scores associated with phrases in textual descriptions of the code description metadata, and each similarity score may indicate a similarity level associated with each of the code with another code in the code dataset.

Referring now to TABLE 3 below, a plurality of similarity scores are illustrated. In the example shown in TABLE 3, the plurality of similarity scores may indicate a level of semantic similarity between the medical code 0BYK0Z0 (of the coding system ICD10PCS) and other medical codes. The textual description of the medical code 0BYK0Z0 may be "Transplantation of Right Lung, Allogeneic, Open Approach."

TABLE 3

Example Similarity Scores

| Coding System | Code | Textual Description | Similarity Score |
|---|---|---|---|
| ICD10PCS | 0BYL0Z0 | Transplantation of Left Lung, Allogeneic, Open Approach | 0.999281 |
| ICD10PCS | 0BYK0Z1 | Transplantation of Right Lung, Syngeneic, Open Approach | 0.986456 |
| ICD10PCS | 0BYL0Z1 | Transplantation of Left Lung, Syngeneic, Open Approach | 0.986001 |
| ICD10PCS | 0UY00Z0 | Transplantation of Right Ovary, Allogeneic, Open Approach | 0.885860 |
| ICD10PCS | 0UY10Z0 | Transplantation of Left Ovary, Allogeneic, Open Approach | 0.884795 |
| ICD10PCS | 0UY00Z1 | Transplantation of Right Ovary, Syngeneic, Open Approach | 0.860558 |
| ICD10PCS | 0UY10Z1 | Transplantation of Left Ovary, Syngeneic, Open Approach | 0.859414 |
| ICD10PCS | 0TY00Z0 | Transplantation of Right Kidney, Allogeneic, Open Approach | 0.848310 |
| ICD10PCS | 0TY10Z0 | Transplantation of Left Kidney, Allogeneic, Open Approach | 0.845184 |
| ICD10PCS | 0BYK0Z2 | Transplantation of Right Lung, Zooplastic, Open Approach | 0.838628 |

As shown in TABLE 3, the semantic machine learning model may identify the semantic similarity between "left" and "right" in the textual descriptions. For example, the medical code 0BYL0Z0 with the textual description "Transplantation of Left Lung, Allogeneic, Open Approach" may have the highest similarly score.

The semantic machine learning model may identify different types of operations (e.g. allogeneic, syngeneic) described in the textual descriptions, as well as different organs (e.g. lung, ovary) described in the textual descriptions. For example, medical codes that contain the word "ovary" in the textual description (for example, medical codes 0UY00Z0 and 0UY10Z0) may have lower similarly scores as compared to similarly scores of medical codes that contain the word "lung" in the textual description (for example, medical codes 0BYK0Z1 and 0BYL0Z1).

In some examples, the plurality of semantic feature vectors may be generated based at least in part on similarity scores. For example, the value of each numeric representation in the feature vector may be determined based on the similarity scores. Continuing from the example shown in TABLE 3 above, the feature vector for the medical code 0BYK0Z0 may comprise ten numeric representations, each corresponding to a code listed in TABLE 3. The value of each numeric representation may be the similarly score of the corresponding code listed in TABLE 3.

While the above example illustrated in TABLE 3 comprises medical codes associated with the same coding system ICD10PCS, it is noted that the scope of the present disclosure is not limited to medical codes in the same coding system. For example, the semantic machine learning model may calculate similarity scores based on textual descriptions associated with medical codes that are related to different coding systems. Similar to those described above, the similarity scores may indicate similarity levels associated with these textual descriptions.

Referring now to TABLE 4 below, a plurality of similarity scores are illustrated. In the example shown in TABLE 4, the plurality of similarity scores may indicate a level of semantic similarity between the medical code 368816007 (of the coding system SNOMEDCT_US) and other medical codes from various coding systems (for example, coding systems SNOMEDCT_US and ICD10PCS). The textual description of the medical code 368816007 may be "entire muscular fascia of eyeball."

In the example shown in TABLE 4, the semantic machine learning model may identify the semantic similarity based on the learned semantic information associated with the textual descriptions. For example, the medical code 86588008 with the textual description "structure of muscular fascia of eyeball" may have the highest similarly score, as its textual description is closest in terms of semantic context with the textual description of the medical code 368816007.

In some examples, a computing entity (such as the feature representation computing entity 105 described above in connection with FIG. 1 and FIG. 2) may include means (such as the processing element 205 of the feature representation computing entity 105 described above in connection with FIG. 2) for generating a semantic feature space based at least in part on the plurality of semantic feature vectors generated by the semantic machine learning model. Referring now to FIG. 9, an example semantic feature space is illustrated.

As shown in FIG. 9, the example semantic feature space 900 may comprise a plurality of semantic feature nodes. Each of the plurality of semantic feature nodes may be associated with a corresponding medical code. In the example as shown in FIG. 9, the nodes may represent medical codes associated with the coding systems ICD10PCS, ICD10CM, and CPT.

As described above, the plurality of semantic feature vectors may capture semantic information associated with the medical codes. In some examples, proximities of semantic feature nodes in the semantic feature space may be based on the semantic information. For example, a proximity between two semantic feature nodes in the semantic feature space may be based at least in part on at least a similarity level associated with the textual descriptions associated with the medical codes represented by the two semantic feature nodes (for example, similarity scores as described above). If there is a high similarity level between the two medical codes, the corresponding semantic feature nodes may be placed closer to one another as compared to semantic feature nodes that are associated with medical codes having a low

TABLE 4

Example Similarity Scores

| Coding System | Code | Textual Description | Similarity Score |
|---|---|---|---|
| SNOMEDCT_US | 86588008 | Structure of muscular fascia of eyeball | 0.88 |
| SNOMEDCT_US | 181772008 | Entire fascia | 0.74 |
| SNOMEDCT_US | 727287005 | Entire phrenicopleural fascia | 0.74 |
| SNOMEDCT_US | 317865002 | Entire clavipectoral fascia | 0.74 |
| SNOMEDCT_US | 279587007 | Entire cremasteric fascia | 0.73 |
| SNOMEDCT_US | 62550004 | Operation on muscle, tendon and fascia of hand | 0.64 |
| ICD10PCS | 0J2TXY | Medical and Surgical @ Subcutaneous Tissue and Fascia @ Change @ Subcutaneous Tissue and Fascia, Trunk @ External @ Other Device | 0.64 |
| SNOMEDCT_US | 260038005 | Entire visceral fascia of pelvis | 0.64 |
| ICD10PCS | 0J2TX | Medical and Surgical @ Subcutaneous Tissue and Fascia @ Change @ Subcutaneous Tissue and Fascia, Trunk @ External | 0.64 |
| SNOMEDCT_US | 732002005 | Entire plantar fascia | 0.64 |
| ICD10PCS | 0JPTX | Medical and Surgical @ Subcutaneous Tissue and Fascia @ Removal @ Subcutaneous Tissue and Fascia, Trunk @ External | 0.64 |
| ICD10PCS | 0JWTX | Medical and Surgical @ Subcutaneous Tissue and Fascia @ Revision @ Subcutaneous Tissue and Fascia, Trunk @ External | 0.64 |
| ICD10PCS | 0JU7 | Medical and Surgical @ Subcutaneous Tissue and Fascia @ Supplement @ Subcutaneous Tissue and Fascia, Back | 0.63 | similarity level. As such, the semantic feature vectors and the corresponding semantic feature space generated by the semantic branch may capture and preserve the semantic information associated with medical codes.

c. Exemplary Structural Branch

As described above, the computing entity may provide code relation metadata (for example, the code relation metadata 616 described above in connection with FIG. 6) associated with a plurality of codes in the code dataset to a structural branch (for example, the structural branch 606 described above in connection with FIG. 6). The code relation metadata may describe one or more relationships between the plurality of codes.

As an example, TABLE 5 below illustrates example relationships between the plurality of example codes described by the example code relation metadata.

TABLE 5

Example Code Relation Metadata

| Coding System | Code 1 | Relationship | Code 2 |
|---|---|---|---|
| ICD10PCS | 0BYK | CHD/ | 0BYK0 |
| ICD10PCS | 0BYK0Z | PAR/ | 0BYK0 |
| ICD10PCS | 0BYK | PAR/ | 0BY |
| ICD10PCS | 0BYK | SIB/ | 0BYC |
| ICD10PCS | 0BYK | SIB/ | 0BYD |
| ICD10PCS | 0BYK | SIB/ | 0BYF |
| ICD10PCS | 0BYK | SIB/ | 0BYG |
| ICD10PCS | 0BYK | SIB/ | 0BYH |
| ICD10PCS | 0BYK | SIB/ | 0BYJ |
| ICD10PCS | 0BYK | SIB/ | 0BYL |
| ICD10PCS | 0BYK | SIB/ | 0BYM |
| ICD10PCS | 0BYK0 | CHD/ | 0BYK0Z |
| ICD10PCS | 0BYK0Z0 | PAR/ | 0BYK0Z |
| ICD10PCS | 0BYK0Z1 | PAR/ | 0BYK0Z |
| ICD10PCS | 0BYK0Z2 | PAR/ | 0BYK0Z |
| ICD10PCS | 0BYK0 | PAR/ | 0BYK |
| ICD10PCS | 0BYK0Z | CHD/ | 0BYK0Z0 |
| ICD10PCS | 0BYK0Z1 | SIB/ | 0BYK0Z0 |
| ICD10PCS | 0BYK0Z2 | SIB/ | 0BYK0Z0 |
| ICD10PCS | 0BYK0Z | CHD/ | 0BYK0Z1 |
| ICD10PCS | 0BYK0Z0 | SIB/ | 0BYK0Z1 |
| ICD10PCS | 0BYK0Z2 | SIB/ | 0BYK0Z1 |
| ICD10PCS | 0BYK0Z | CHD/ | 0BYK0Z2 |
| ICD10PCS | 0BYK0Z0 | SIB/ | 0BYK0Z2 |
| ICD10PCS | 0BYK0Z1 | SIB/ | 0BYK0Z2 |

In the example shown in TABLE 5 above, the plurality of example codes may be associated with a plurality of medical codes that are formatted in accordance with the same coding system (i.e. the coding system ICD10PCS). When generating the code dataset, the computing entity (such as the feature representation computing entity 105 described above in connection with FIG. 1 and FIG. 2) may include means (such as the processing element 205 of the feature representation computing entity 105 described above in connection with FIG. 2) for retrieving code relation metadata associated with each medical code from a data storage device (such as a data storage device that stores information related to medical codes of the coding system ICD10PCS), and for extracting relationships between medical codes from the code relation metadata.

In the example shown in TABLE 5 above, the relationships may indicate whether a medical code (i.e. "Code 2") is a child (i.e. "CHD/"), a parent (i.e. "PAR/") or a sibling (i.e. SIB/") of another medical code (i.e. "Code 1") in a hierarchical structure. For example, the medical code 0BYK0 is a child code of the medical code 0BYK. As another example, the medical code 0BYK0 is a parent code of the medical code 0BYK0Z. As another example, the medical code 0BYC is a sibling code of the medical code 0BYK.

While the examples illustrated in TABLE 5 comprise medical codes in accordance with the same coding system, as described above, the plurality of medical codes in the code dataset may be associated with different coding systems. As another example, TABLE 6 below illustrates example numbers of relationships between medical codes within the same coding system and medical codes among different coding systems.

TABLE 6

Example Number Of Relationships

| Coding System 1 | Coding System 2 | Number Of Relationships Between Coding System 1 And Coding System 2 |
|---|---|---|
| CPT | CPT | 499084 |
| CPT | ICD10PCS | 1 |
| CPT | SNOMEDCT_US | 46662 |
| ICD10CM | ICD10CM | 650046 |
| ICD10CM | SNOMEDCT_US | 97586 |
| ICD10PCS | CPT | 27 |
| ICD10PCS | ICD10PCS | 951403 |
| ICD10PCS | SNOMEDCT_US | 161 |
| SNOMEDCT_US | CPT | 40805 |
| SNOMEDCT_US | ICD10CM | 69085 |
| SNOMEDCT_US | ICD10PCS | 20 |
| SNOMEDCT_US | SNOMEDCT_US | 4807260 |

As an example, a plurality of example codes in a code dataset may be associated with a plurality of medical codes that are formatted in accordance with the different coding system (i.e. the coding systems CPT, ICD10CM, ICD10PCS, and SNOMEDCT_US). In this example, the computing entity (such as the feature representation computing entity 105 described above in connection with FIG. 1 and FIG. 2) may include means (such as the processing element 205 of the feature representation computing entity 105 described above in connection with FIG. 2) for retrieving code relation metadata associated with each medical code from one or more data storage devices (such as one or more data storage devices that store information related to medical codes of the coding systems CPT, ICD10CM, ICD10PCS, and SNOMEDCT_US), and for extracting relationships associated with medical codes from the code relation metadata.

Referring now to FIG. 10, an example hierarchical visualization 1000 is illustrated. In particular, the example hierarchical visualization 1000 may comprise a plurality of graph nodes, and each graph node may represent a medical code of a plurality of medical codes (for example, one of the medical codes listed in TABLE 5). The graph nodes may be connected in a hierarchical structure based on relationships between the medical codes as indicated by the code relation metadata. For example, the graph node that represents the medical code 0BYK is shown as a parent node of the graph node that represents the medical code 0BYK0, which reflects that the medical code 0BYK is a parent code of the medical code 0BYK0.

In some examples, the similarities of textual description associated with the medical codes may correlate to the relationships between the medical codes. For example, TABLE 7 below illustrates similar codes for the medical code 0BYK0Z0 (of ICD10PCS medical coding system). The medical code 0BYK0Z0 may represent "Transplantation of Right Lung, Allogeneic, Open Approach."

TABLE 7

Example Similar Codes

| Coding System | Code | Textual Description | Similarity Score |
|---|---|---|---|
| ICD10PCS | 0BYK0Z1 | Transplantation of Right Lung, Syngeneic, Open Approach | 0.944415 |
| ICD10PCS | 0BYK0Z2 | Transplantation of Right Lung, Zooplastic, Open Approach | 0.821550 |
| ICD10PCS | 0BYK0Z | Medical and Surgical @ Respiratory System @ Transplantation @ Lung, Right @ Open @ No Device | 0.779178 |
| ICD10CM | S63.496 | Traumatic rupture of other ligament of right little finger at metacarpophalangeal and interphalangeal joint | 0.553407 |
| ICD10PCS | 0L8T4 | Medical and Surgical @ Tendons @ Division @ Ankle Tendon, Left @ Percutaneous Endoscopic | 0.534834 |
| ICD10CM | S63.496S | Traumatic rupture of other ligament of right little finger at metacarpophalangeal and interphalangeal joint, sequela | 0.525632 |
| ICD10CM | S63.496D | Traumatic rupture of other ligament of right little finger at metacarpophalangeal and interphalangeal joint, subsequent encounter | 0.520810 |
| ICD10PCS | 03754F6 | Dilation of Right Axillary Artery, Bifurcation, with Three Intraluminal Devices, Percutaneous Endoscopic Approach | 0.518186 |
| ICD10PCS | DD129BZ | High Dose Rate (HDR) Brachytherapy of Duodenum using Palladium 103 (Pd-103) | 0.517084 |
| ICD10CM | S63.497 | Traumatic rupture of other ligament of left little finger at metacarpophalangeal and interphalangeal joint | 0.510141 |

In the example shown in TABLE 7 above, the most similar medical codes to the medical code 0BYK0Z0 are medical codes 0BYK0Z1 and 0BYK0Z2. As shown in FIG. 10, the medical codes 0BYK0Z1 and 0BYK0Z2 are sibling medical codes of the medical code 0BYK0Z0. As such, the one or more relationships between the plurality of codes may additionally, or alternatively, be determined based on the textual descriptions.

While the example hierarchical visualization 1000 illustrated in FIG. 10 is associated with medical codes within the same coding system, it is noted that the scope of the present disclosure is not limited to the codes being in the same coding system. Referring now to FIG. 11, an example hierarchical visualization 1100 is illustrated. The example hierarchical visualization 1100 may comprise graph nodes that represent medical codes in a variety of coding systems, such as ICD10PCS, ICD10CM, CPT and SNOMED The graph nodes may be connected to one another based on the relationships associated with the corresponding medical codes. In this example, the graph machine learning model may analyze each graph node in the hierarchical visualization 1100, and may extract structural information from the graph nodes in generating the plurality of structural feature vectors, similar to those described above.

As described above, the structural branch may comprise a structural machine learning model (for example, the structural machine learning model 614 described above in connection with FIG. 6). The structural machine learning model may generate a plurality of structural feature vectors based on the code relation metadata, and the plurality of structural feature vectors may represent structural information associated with codes.

For example, the structural machine learning model may comprise a graph machine learning model (such as, but not limited to, knowledge graph models such as ComplEx via the implementation of Pytorch Big Graph, TransE, RotatE, LiteralE, graph convolutional networks such as GCN, GraphSAGE, and/or the like). The graph machine learning model may extract structural information from the relationships between the plurality of codes (and/or from features associated with each code), and may generate the plurality of structural feature vectors based on the relationships.

In some examples, the graph machine learning model may determine a density level of a relationship between a corresponding graph node and another graph node, and may determine a value for a numeric representation in a structural feature vector for a corresponding code of the corresponding graph node based on the density level. For example, the graph machine learning model may determine a density level based on whether two graph nodes are directly connected (for example, a parent-child connection or a sibling connection) in the hierarchical structure. The graph machine learning model may determine a high density level if the corresponding graph nodes are directly connected, as compared to graph nodes that are indirectly connected or not connected. Referring to the example shown in FIG. 10, when generating a feature vector for the medical code 0BYK, the graph machine learning model may assign a high numeric value for the numeric representation that represents a relationship between the medical code 0BYK and the medical code 0BYK0, as the medical code 0BYK0 is a child of the medical code 0BYK.

As another example, the graph machine learning model may determine the density level based on the number of intermediate graph nodes between two graph nodes in the hierarchical structure. The higher the number of intermediate graph nodes, the lower the density level. Referring to the example shown in FIG. 10, when generating a feature vector for the medical code 0BYK, the graph machine learning model may assign a high numeric value for the numeric representation that represents a relationship with the medical code 0BYK0, as compared to the numeric value for the numeric representation that represents a relationship with the medical code 0BYK0Z1. As shown in FIG. 10, there is no intermediate graph node between the graph node that represents the medical code 0BYK and the graph node that represents the medical code 0BYK0, and there are two intermediate graph nodes between the graph node that represents the medical code 0BYK and the graph node that represents the medical code 0BYK0Z1.

In some examples, a computing entity (such as the feature representation computing entity 105 described above in connection with FIG. 1 and FIG. 2) may include means (such as the processing element 205 of the feature representation computing entity 105 described above in connection with FIG. 2) for generating a structural feature space based at least in part on the plurality of structural feature vectors generated by the structural machine learning model. Referring now to FIG. 12, an example structural feature space is illustrated.

As shown in FIG. 12, the example structural feature space 1200 may comprise a plurality of structural feature nodes. Each of the plurality of structural feature nodes may be associated with a corresponding medical code.

As described above, the plurality of structural feature vectors may capture structural information (for example, relations and hierarchies) associated with the medical codes. In some examples, proximities of structural feature nodes in the structural feature space may be based on the one or more relationships described in the code relation metadata. For example, a proximity between two nodes in the feature space may be based at least in part on the density level of relationships associated with the medical codes represented by the two nodes. If there is a direct connection between the two medical codes (for example, a parent-child connection or a sibling connection), the corresponding nodes may be placed closer to one another as compared to nodes that are associated with medical codes having an indirect connection or no connection. As such, the structural feature vectors and the corresponding structural feature space generated by the structural branch may capture and preserve the structural information associated with medical codes.

d. Exemplary Prediction Generation

As described above, various example multi-paradigm feature vectors of the present disclosure may be provided to a prediction model for generating one or more predictions associated with a predictive entity.

For example, the predictive entity may be a medical claim. In accordance with various embodiments of the present disclosure, a plurality of multi-paradigm feature vectors may be generated based on medical codes associated with the medical claim, and the plurality of multi-paradigm feature vectors may capture both the semantic information and the structural information of the medical codes.

Example multi-paradigm feature vectors generated in accordance with the present disclosure may produce features that have superior data representation capabilities than other techniques (such as encoding techniques and embedding techniques described above). For example, these multi-paradigm feature vectors may allow complete medical code representation, unlike techniques that rely on claim data (e.g. data-driven FWAE detection techniques), which are limited to codes that exist in the data and unable to handle codes that were never seen in the training data.

Referring now to FIG. 13, example performance curves of outputs from two prediction models are illustrated. In particular, the prediction models may be unsupervised machine learning models that are configured to detect medical fraud, waste, abuse and error (referred to as "unsupervised FWAE model" herein). The y-axis may indicate anomaly scores (i.e. outputs from the unsupervised FWAE model) while the x-axis may indicate the number of claims (i.e. data points that the unsupervised FWAE model is configured to analyze). In the example shown in FIG. 13, the anomaly scores for the one thousand (1000) most suspicious data points are illustrated.

The curve 1301 may be associated with a baseline model that does not implement embodiments of the present disclosure. For example, the curve 1301 may be outputs from a prediction model that receive inputs based on simple word embedding of the medical codes, instead of the multi-paradigm feature vectors generated in accordance with examples of the present disclosure.

In contrast, the curve 1303 may be associated with a prediction model based on embodiments of the present disclosure. For example, the curve 1303 may be outputs from a prediction model that receive inputs based on the multi-paradigm feature vectors generated in accordance with the present disclosure.

As shown in FIG. 13, when multi-paradigm feature vectors in accordance with examples of the present disclosure are provided as input to an unsupervised FWAE model, the unsupervised FWAE model may produce anomaly scores (i.e. the curve 1303) that decrease at a sharper rate than that of anomaly scores (i.e. the curve 1301) that are generated by an unsupervised FWAE model based on input that do not implement examples of the present disclosure. In other words, when the multi-paradigm feature vectors are provided to the unsupervised FWAE model, the unsupervised FWAE model may provide a feature space where the outliners have high anomaly scores (i.e. medical claims have high likelihoods of fraud, water, abuse, and error) than the normal data points (i.e. medical claims that have low likelihoods of fraud, water, abuse, and error). As such, the multi-paradigm feature vectors may enable the unsupervised FWAE model to better distinguish anomalies data from normal data.

As described above, the multi-paradigm feature vectors may be implemented in the context of supervised machine learning models that are configured to detect medical fraud, waste, abuse and error (referred to as "supervised FWAE model" herein). Referring now to TABLE 8 below, examples performance indicators of three supervised FWAE models are illustrated.

TABLE 8

Example Performance Indicators

| Model Number | Precision | Recall | ROC-UAC |
|---|---|---|---|
| 1 | 0.286 | 0.587 | 0.611 |
| 2 | 0.289 | 0.612 | 0.622 |
| 3 | 0.282 | 0.644 | 0.617 |

In the example shown in TABLE 8, the first supervised FWAE model (model number 1) may be trained based on feature vectors from only the structural branch of the present disclosure. The second supervised FWAE model (model number 2) may be trained based on feature vectors from only the semantic branch of the present disclosure. The third supervised FWAE model (model number 3) may be trained based on feature vectors from both the semantic branch and the structural branch (i.e. the multi-paradigm feature vectors). As shown in TABLE 8, the supervised FWAE model that is trained based on the multi-paradigm feature vectors in accordance with examples of the present disclosure (model number 3) may produce a good ROC-AUC score with consistent precision and recall, and may therefore improve the prediction distribution for normal claims and FWAE claims (which may better distinguish FWAE claims from normal claims).

V. CONCLUSION

Many modifications and other embodiments of the disclosure set forth herein will come to mind to one skilled in the art to which this disclosure pertain having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. An apparatus for programmatically generating multi-paradigm feature representations, the apparatus comprising at least one processor and at least one non-transitory memory comprising a computer program code, the at least one non-transitory memory and the computer program code configured to, with the at least one processor, cause the apparatus to:
  generate a code dataset comprising a plurality of codes associated with a predictive entity, wherein a first portion of the plurality of codes is associated with a first coding system, wherein (i) a second portion of the plurality of codes is associated with a second coding system different from the first coding system, (ii) the plurality of codes is associated with code description metadata and code relation metadata, (iii) the code description metadata for a code comprises a textual description of the code, and (iv) the code relation metadata describes one or more relationships between the plurality of codes;
  generate, by processing the code description metadata for each code of the plurality of codes using a semantic machine learning model, a plurality of semantic feature vectors based at least in part on the code description metadata, wherein (i) the plurality of semantic feature vectors comprises a semantic feature vector for each code of the plurality of codes, and (ii) each semantic feature vector that is associated with a code comprises numeric representations of one or more phrases used in the textual description for the code;
  generate, by processing the code relation metadata using a structural machine learning model, a plurality of structural feature vectors based at least in part on the code relation metadata;
  generate a plurality of multi-paradigm feature vectors based at least in part on the plurality of semantic feature vectors and the plurality of structural feature vectors;
  generate a prediction for the predictive entity by processing the plurality of multi-paradigm feature vectors using a prediction model; and
  perform one or more prediction-based actions based at least in part on the prediction.

2. The apparatus of claim 1, wherein the plurality of codes are associated with a plurality of medical codes.

3. The apparatus of claim 2, wherein the plurality of medical codes are associated with a same coding system.

4. The apparatus of claim 1, wherein the semantic machine learning model comprises at least one natural language processing (NLP) machine learning model.

5. The apparatus of claim 4, wherein the at least one non-transitory memory and the computer program code are configured to, with the at least one processor, cause the apparatus to further:
  generate a semantic feature space comprising a plurality of semantic feature nodes based at least in part on the plurality of semantic feature vectors, wherein (i) each of the plurality of semantic feature nodes is associated with a corresponding code of the plurality of codes, and (ii) proximities between the plurality of semantic feature nodes are based at least in part on a similarity level associated with the textual description of each corresponding code.

6. The apparatus of claim 1, wherein the structural machine learning model comprises a graph machine learning model.

7. The apparatus of claim 6, wherein the at least one non-transitory memory and the computer program code are configured to, with the at least one processor, cause the apparatus to further:
  generate a structural feature space comprising a plurality of structural feature nodes based at least in part on the plurality of structural feature vectors, wherein (i) each of the plurality of structural feature nodes is associated with a corresponding code of the plurality of codes, and (ii) proximities between the plurality of structural feature nodes are based at least in part on the one or more relationships described in the code relation metadata.

8. The apparatus of claim 7, wherein, when generating the plurality of multi-paradigm feature vectors, the at least one non-transitory memory and the computer program code are configured to, with the at least one processor, cause the apparatus to further:
  merge the plurality of semantic feature vectors and the plurality of structural feature vectors.

9. A computer-implemented method for programmatically generating multi-paradigm feature representations, comprising:
  generating a code dataset comprising a plurality of codes associated with a predictive entity, wherein a first portion of the plurality of codes is associated with a first coding system, wherein (i) a second portion of the plurality of codes is associated with a second coding system different from the first coding system, (ii) the plurality of codes is associated with code description metadata and code relation metadata, (iii) the code description metadata for a code comprises a textual description of the code, and (iv) the code relation metadata describes one or more relationships between the plurality of codes;
  generating, by processing the code description metadata for each code of the plurality of codes using a semantic machine learning model, a plurality of semantic feature vectors based at least in part on the code description metadata, wherein (i) the plurality of semantic feature vectors comprises a semantic feature vector for each code of the plurality of codes, and (ii) each semantic feature vector that is associated with a code comprises numeric representations of one or more phrases used in the textual description for the code;
  generating, by processing the code relation metadata using a structural machine learning model, a plurality of structural feature vectors based at least in part on the code relation metadata;
  generating a plurality of multi-paradigm feature vectors based at least in part on the plurality of semantic feature vectors and the plurality of structural feature vectors;
  generating a prediction for the predictive entity by processing the plurality of multi-paradigm feature vectors using a prediction model; and
  performing one or more prediction-based actions based at least in part on the prediction.

10. The computer-implemented method of claim 9, wherein the plurality of codes are associated with a plurality of medical codes.

11. The computer-implemented method of claim 10, wherein the plurality of medical codes are associated with a same coding system.

12. The computer-implemented method of claim 9, wherein the semantic machine learning model comprises at least one natural language processing (NLP) machine learning model.

13. The computer-implemented method of claim 12, further comprising: generating a semantic feature space comprising a plurality of semantic feature nodes based at least in part on the plurality of semantic feature vectors, wherein (i) each of the plurality of semantic feature nodes is associated with a corresponding code of the plurality of codes, and (ii)

proximities between the plurality of semantic feature nodes are based at least in part on a similarity level associated with the textual description of each corresponding code.

14. The computer-implemented method of claim 9, wherein the structural machine learning model comprises a graph machine learning model.

15. The computer-implemented method of claim 14, further comprising:
generating a structural feature space comprising a plurality of structural feature nodes based at least in part on the plurality of structural feature vectors, wherein (i) each of the plurality of structural feature nodes is associated with a corresponding code of the plurality of codes, and (ii) proximities between the plurality of structural feature nodes are based at least in part on the one or more relationships described in the code relation metadata.

16. A computer program product for programmatically generating multi-paradigm feature representations, the computer program product comprising at least one non-transitory computer-readable storage medium having computer-readable program code portions stored therein, the computer-readable program code portions comprising an executable portion configured to:
generate a code dataset comprising a plurality of codes associated with a predictive entity, wherein a first portion of the plurality of codes is associated with a first coding system, wherein (i) a second portion of the plurality of codes is associated with a second coding system different from the first coding system, (ii) the plurality of codes is associated with code description metadata and code relation metadata, (iii) the code description metadata for a code comprises a textual description of the code, and (iv) the code relation metadata describes one or more relationships between the plurality of codes;
generate, by processing the code description metadata for each code of the plurality of codes using a semantic machine learning model, a plurality of semantic feature vectors based at least in part on the code description metadata, wherein (i) the plurality of semantic feature vectors comprises a semantic feature vector for each code of the plurality of codes, and (ii) each semantic feature vector that is associated with a code comprises numeric representations of one or more phrases used in the textual description for the code;
generate, by processing the code relation metadata using a structural machine learning model, a plurality of structural feature vectors based at least in part on the code relation metadata;
generate a plurality of multi-paradigm feature vectors based at least in part on the plurality of semantic feature vectors and the plurality of structural feature vectors;
generate a prediction for the predictive entity by processing the plurality of multi-paradigm feature vectors using a prediction model; and
perform one or more prediction-based actions based at least in part on the prediction.

17. The computer program product of claim 16, wherein the plurality of codes are associated with a plurality of medical codes.

18. The computer program product of claim 16, wherein the semantic machine learning model comprises at least one natural language processing (NLP) machine learning model.

* * * * *